US008247420B2

(12) United States Patent
Bhat et al.

(10) Patent No.: US 8,247,420 B2
(45) Date of Patent: Aug. 21, 2012

(54) COMPOSITIONS, SYNTHESIS, AND METHODS OF USING QUINOLINONE BASED ATYPICAL ANTIPSYCHOTIC AGENTS

(75) Inventors: Laxminarayan Bhat, Cupertino, CA (US); Prabhu P. Mohapatra, San Jose, CA (US); Seema Rani Bhat, Cupertino, CA (US)

(73) Assignee: Reviva Pharmaceuticals, Inc., San Jose, CA (US)

( * ) Notice: Subject to any disclaimer, the term of this patent is extended or adjusted under 35 U.S.C. 154(b) by 615 days.

(21) Appl. No.: 12/124,985

(22) Filed: May 21, 2008

(65) Prior Publication Data
US 2008/0293736 A1 Nov. 27, 2008

Related U.S. Application Data

(60) Provisional application No. 60/939,262, filed on May 21, 2007.

(51) Int. Cl.
*A61K 31/497* (2006.01)
*C07D 401/12* (2006.01)
(52) U.S. Cl. .................................. 514/253.04; 544/363
(58) Field of Classification Search ............. 514/253.04; 544/363
See application file for complete search history.

(56) References Cited

U.S. PATENT DOCUMENTS

| | | | |
|---|---|---|---|
| 3,845,770 | A | 11/1974 | Theeuwes et al. |
| 3,916,899 | A | 11/1975 | Theeuwes et al. |
| 4,746,661 | A | 5/1988 | Lattrell et al. |
| 5,112,598 | A | 5/1992 | Biesalski |
| 5,556,611 | A | 9/1996 | Biesalski |
| 5,698,155 | A | 12/1997 | Grosswald et al. |
| 6,066,666 | A | 5/2000 | Covey et al. |
| 6,346,528 | B1 | 2/2002 | Yelle et al. |
| 6,432,985 | B2 | 8/2002 | Alanine et al. |
| 2003/0027823 | A1 | 2/2003 | Cereda et al. |
| 2005/0043309 | A1 | 2/2005 | Clark et al. |
| 2005/0261308 | A1 | 11/2005 | Repke et al. |
| 2006/0083676 | A1 | 4/2006 | Lesage et al. |
| 2007/0004707 | A1 | 1/2007 | Ramamoorthy |

FOREIGN PATENT DOCUMENTS

| | | |
|---|---|---|
| EP | 0367141 | 5/1990 |
| EP | 0900792 | 3/1999 |
| GB | 2017701 | 10/1979 |
| WO | WO 03/064393 A1 | 8/2003 |
| WO | WO-2004026864 | 4/2004 |
| WO | WO 2004/063162 A1 | 7/2004 |
| WO | WO 2004/099152 A1 | 11/2004 |
| WO | WO 2006/030446 A1 | 3/2006 |
| WO | WO 2006/038220 A1 | 4/2006 |

OTHER PUBLICATIONS

PCT International Search Report and Written Opinion, PCT/US08/64433, Aug. 19, 2008, 13 pages.
Bamba, M. et al., "Release Mechanisms in Gelforming Sustained Release Preparations," International Journal of Pharmaceutics, 1979, pp. 307-315, vol. 2.
Burstein, E.S. et al., "Intrinsic Efficacy of Antipsychotics at Human $D_2$, $D_3$, and $D_4$ Dopamine Receptors: Identification of the Clozapine Metabolite N-Desmethylclozapine as a $D_2/D_3$ Partial Agonist," Journal of Pharmacology and Experimental Therapeutics 2005, pp. 1278-1287, vol. 315, No. 3.
Conley, R.R. et al., "Drug-Drug Interactions Associated with Second-Generation Antipsychotics: Considerations for Clinicians and Patients," Psychopharmacology Bulletin, 2007, pp. 77-97, vol. 40, No. 1.
Crespi, C.L., "Higher-Throughput Screening with Human Cytochromes P450," Current Opinion in Drug Discovery & Development, 1999, pp. 15-19, vol. 2, No. 1.
Di Pietro, N.C. et al., "Dopamine and Serotonin Interactions in the Prefrontal Cortex: Isights on Antipsychotic Drugs and Their Mechanism of Action," Pharmacopsychiatry, 2007, pp. S27-S33, vol. 40, Suppl. 1.
During, M.J. et al., "Controlled Release of Dopamine from a Polymeric Brain Implant: In Vivo Characterization," Annals of Neurolology, Apr. 1989, pp. 351-356, vol. 25, No. 4.
Favreau, L.V. et al., "Improved Reliability of the Rapid Microtiter Plate Assay Using Recombinant Enzyme in Predicting CYP2D6 Inhibition in Human Liver Microsomes," Drug Metabolism and Disposition, 1989, pp. 436-439, vol. 27, No. 4.
Fioravanzo, E. et al., "General and Independent Approaches to Predict HERG Affinity Values," Internet Electronic Journal of Molecular Design, Sep. 2005,pp. 625-646, vol. 4, No. 9.
Glick, S.D. et al., "Enantioselective Behavioral Effects of Sibutramine Metabolites," European Journal of Pharmacology, 2000, pp. 93-102, vol. 397.
Goodson, J.M. "Dental Applications," Medical Applications of Controlled Release, Langer and Wise (eds.), Wiley, New York, 1984, pp. 115-138.
Gundlach, A.L. et al., "$^{125}$I-Spiperone: A Novel Ligand for $D_2$ Dopamine Receptors," Life Sciences, 1984, pp. 1984-1988, vol. 35.
Houston, J.B., "Utility of in Vitro Drug Metabolism Data in Predicting in Vivo Metabolic Clearance," Biochemical Pharmacology, 1994, pp. 1467-1469, vol. 47, No. 9.
Howard, M.A. et al., "Intracerebral Drug Delivery in Rats with Lesion-Induced Memory Deficits," J. Neurosurg., 1989, pp. 105-112, vol. 71. Hoyer, D. et al., "Molecular Pharmacology of 5-$HT_1$ and 5-$HT_2$ Recognition Sites in Rat and Pig Brain Membranes: Radioligand Binding Studies with [$^3$H]5-HT, [$^3$H]8-OH-DPAT, (-)[$^{125}$I]Iodocyanopindolol, [$^3$H]Mesulergine and [$^3$H]Ketanserin," European Journal of Pharmacology, 1985, pp. 13-23, vol. 118.
International Search Report and Written Opinion, PCT/US08/64433, Aug. 19, 2008, 13 pages.
Jarvie, K.R. et al., "Molecular Cloning, Stable Expression and Desensitization of the Human Dopamine D1B / D5 Receptor," Journal of Receptor Research, 1993, pp. 573-590, vol. 13 No. 1-4.
Korzekwa, K.R. et al., "Evaluation of Atypical Cytochrome P450 Kintecs with Two-Substrate Models: Evidence That Multiple Substrates Can Simultaneously Bind to Cytochrome P450 Active Sites," Biochemistry, 1998, pp. 4137-4147, vol. 37.
Langer, R., "New Methods of Drug Delivery," Science, Sep. 28, 1990, pp. 1527-1533, vol. 249.
Langer, R. et al., "Chemical and Physical Structure of Polymers as Carriers for Controlled Release of Bioactive Agents: A Review," Journal of Macromolecular Science Reviews in Macromolecular Chemistry and Physics, 1983, pp. 61-126, vol. 23, No. 61.
Levy, R. et al., "Inhibition of Calcification of Bioprosthetic Heart Valves by Local Controlled-Release Diphosphonate," Science, Apr. 12, 1985, pp. 190-192, vol. 228, No. 4696.

(Continued)

*Primary Examiner* — James O Wilson
*Assistant Examiner* — Ebenezer O Sackey
(74) *Attorney, Agent, or Firm* — Perkins Coie LLP.; Viola T. Kung

(57) ABSTRACT

The present invention provides novel quinolinone derivatives which can be advantageously used for treating schizophrenia and related psychoses such as acute manic, bipolar disorder, autistic disorder, and depression.

23 Claims, No Drawings

OTHER PUBLICATIONS

Leysen, J.E. et al., "[$^3$H]Ketanserin (R 41 468), a Selective $^3$H-Ligand for Serotonin$_2$ Receptor Binding Sites," Molecular Pharmacology, 1982, pp. 301-314, vol. 21.

Martin, G.R. et al., "Receptors for 5-Hydroxytryptamine: Current Perspectives on Classification and Nomenclature," Neuropharmacology, 1994, pp. 261-273, vol. 33, No. 3/4.

Miyamoto, S. et al., "Treatments for Schizophrenia: A Critical Review of Pharmacology and Mechanisms of Action of Antipsychotic Drugs," Molecular Psychiatry, 2005, pp. 79-104, vol. 10.

Mulder, H. et al., "Prevalence of Patients Using Drugs Metabolized by Cytochrome P450 2D6 in Different Populations: a Cross-Sectional Study," The Annals of Pharmacotherapy, Mar. 2007, pp. 408-413, vol. 41, No. 3.

Oshiro, Y. et al., "Novel Antipsychotic Agents with Dopamine Autoreceptor Agonist Properties: Synthesis and Pharmacology of 7-[4-(4-Phenyl-1-piperazinyl)butoxy]-3,4-dihydro-2(1$H$)-quinolinone Derivatives," J. Med. Chem., 1998, pp. 658-667, vol. 41.

Roden, D. M. et al. "Genetics of Acquired Long QT Syndrome," The Journal of Clinical Investigation, Aug. 2005, pp. 2025-2032, vol. 115, No. 8.

Salama, I. et al., "Structure-Selectivity Investigations of D$_2$-Like Receptor Ligands by CoMFA and CoMSIA Guiding the Discovery of D$_3$ Selective PET Radioligands," J. Med. Chem., 2007, pp. 489-500, vol. 50.

Saudek, C.D. et al., "A Preliminary Trial of the Programmable Implantable Medication System for Insulation Delivery," The New England Journal of Medicine, Aug. 31, 1989, pp. 574-579, vol. 321, No. 9.

Schoeffter, P. et al., "How Selective is GR 43175? Interactions with Functional 5-HT$_{1A}$, 5-HT$_{1B}$, 5-HT$_{1C}$ and 5-HT$_{1D}$ Receptors," Naunyn-Schmiedeberg's Arch. Pharmac., 1989, pp. 135-138, vol. 340.

Sefton, M.V., "Implantable Pumps," Critical Reviews in Biomedical Engineering, 1987, pp. 201-240, vol. 14, Issue 3.

Snyder, S.H., "A Complex in Psychosis," Nature, Mar. 6, 2008, pp. 38-39, vol. 452, Issue No. 7183.

Stark, A.D. et al., "Interaction of the Novel Antipsychotic Aripiprazole with 5-HT$_{1A}$ and 5-HT$_{2A}$ Receptors: Functional Receptor-Binding and In Vivo Electrophysiological Studies," Psychopharmacology 2007, 190, pp. 373-382.

Verma, R.K. et al., "Osmotically Controlled Oral Drug Delivery," Drug Development and Industrial Pharmacy, 2000, pp. 695-708, vol. 26, No. 7.

Zhou, J. et al., "Novel Potent Human Ether-à-Go-Go-Related Gene (hERG) Potassium Channel Enhancers and Their in Vitro Antiarrhythmic Activity," Molecular Pharmacology, 2005, pp. 876-884, vol. 68, No. 3.

New Zealand Examination Report, New Zealand Application No. 582124, Oct. 22, 2010, 2 pages.

Supplementary European Search Report dated Jan. 17, 2012 for Application No. EP 08756096.

COMPOSITIONS, SYNTHESIS, AND METHODS OF USING QUINOLINONE BASED ATYPICAL ANTIPSYCHOTIC AGENTS

CROSS-REFERENCE TO RELATED APPLICATIONS

This application claims the benefit of U.S. Provisional Patent Application No. 60/939,262, filed on May 21, 2007, and which is herein incorporated by reference in its entirety.

FIELD OF THE INVENTION

The present invention relates to compositions of quinolinone derivatives, synthesis of quinolinone derivatives, and methods of using quinolinone derivatives. The present invention more particularly relates to synthesis, compositions and methods of using quinolinone based compounds which are useful for the pharmacological treatment of schizophrenia and related psychoses such as acute manic, bipolar disorder, autistic disorder and depression.

BACKGROUND OF THE INVENTION

Medications used to treat psychotic disorders are called antipsychotics. Typical antipsychotics (sometimes referred to as conventional antipsychotics) are class of first generation antipsychotic drugs and used to treat psychosis including schizophrenia. The typical antipsychotics include chlorpromazine (THORAZINE®), fluphenazine (PROLIXIN®), haloperidol (HALDOL®), thiothixene (NAVANE®), trifluoroperazine (STELAZINE®), perphenazine (TRILAFON®), and thioridazine (MELLARIL®). The second generation antipsychotics introduced in the 1990's are called atypical antipsychotics. Compared to the first generation antipsychotics, the atypical antipsychotics appear to be equally effective in reducing the positive symptoms like hallucinations and delusions but may be better than the typical antipsychotics at relieving the negative symptoms of schizophrenia such as apathy, withdrawal, emotional depression and the like. The atypical antipsychotics currently in clinical use include Aripiprazole (ABILIFY®), clozapine (CLOZARIL®), risperidone (RISPERDAL®), olanzapine (ZYPREXA®), quetiapine (SEROQUEL®), and ziprasidone (GEODON®).

Atypical antipsychotics have diminished propensity to cause extrapyramidal symptoms (EPS) and tardive dyskinesia (TD) than typical antipsychotics. Additional benefits associated with the atypical antipsychotics include better treatment of negative symptoms, better compliance, possible benefits for cognitive impairments, and lower rates of relapse. Within the class of atypical antipsychotics, however, differences exist both in efficacy and side effects. Clozapine does not cause EPS, and is clearly more effective than all other antipsychotics used in humans to date. It is however a life-altering drug, because of its side effects and need for continual medical monitoring, in some countries, for agranulocytosis. This has markedly limited its use. The other atypical antipsychotics with the greatest amount of efficacy data are risperidone and olanzapine. These drugs are the most commonly used first-line antipsychotics today. This is warranted because they are more clinically effective than conventional drugs and much easier to use than clozapine. However, both risperidone and olanzapine are limited by side effects. Risperidone causes prolactin elevations, dose-dependant EPS and some weight gain. Olanzapine use is associated with much more weight gain in addition to lipid and glucose abnormalities. Qetiapine and Ziprasidone may be safer alternatives to risperidone and olanzapine but these drugs do not appear to be as clinically effective as the other atypical antipsychotics. Aripiprazole is one of a new generation of atypical antipsychotic drugs approved by the FDA for the treatment of schizophrenia in November 2002 (Satyanarayana, C. et al. WO 2006/030446; Tsujimori, H. et al. WO 2004/063162; Salama, P. et al. WO 2004/099152; Wikstorm, H. et al. WO 2003/064393). It was approved for the treatment of acute mania and mixed episode associated with bipolar disorder in March 2005. Aripiprazole does not differ greatly from other atypical antipsychotics with respect to treatment response, efficacy and tolerability.

Atypical antipsychotics are increasingly being used in children and adolescents for a variety of psychiatric conditions. Conditions for which atypical antipsychotics are prescribed include bipolar disorder, psychotic depression, schizophrenia, pervasive developmental disorders, attention-deficit/hyperactivity disorder (ADHD), oppositional defiant disorder (ODD), and conduct disorder. They are also used symptomatically to treat rage, insomnia, and anorexia. Younger patients appear to be at a higher risk of adverse effects associated with the treatment of atypical antipsychotics.

In general, atypical antipsychotics share many of the side effects of typical antipsychotics, including sedation, akathisia, weight gain, extrapyramidal symptoms (EPS), neuromalignant syndrome, and tardive dyskinesia; longer experience with them have shown that new risks need to be considered, such as metabolic syndromes and QTc prolongation. QTc prolongation is known to have potential liability to produce fatal cardiac arrhythmias of Torsades de Pointes (TdP). Drug induced adverse metabolic effects such as weight gain, lipid abnormalities, and diabetes mellitus have been identified as a major risk factor for various medical disorders that might be responsible for some of the increased morbidity and mortality rates in psychotic patients treated with atypical antipsychotics.

Off-target pharmacology and drug to drug interactions are mainly responsible for most of the adverse side effects associated with the atypical antipsychotics. All the atypical antipsychotic drugs currently being used for the treatment of schizophrenia and related psychotic disorders have poor therapeutic target selectivity. For example, one of the most widely prescribed atypical antipsychotic drugs, Olanzapine and the most effective atypical antipsychotic drug, clozapine are reported to have significant activities against more than 12 receptors such as dopamine ($D_1$, $D_2$, $D_3$ and $D_4$), serotonin (5-$HT_{2A}$, 5-$HT_{2C}$, 5-$HT_6$, and 5-$HT_7$), adrenergic (alpha 1 and alpha 2), histamine ($H_1$), muscarinic ($M_1$), Dopamine transporter (DAT) and norepinephrine transporter (NET) receptors (Miyamoto et al., Molecular Psychiatry, 2005, 10, 79). Similarly, the other FDA approved atypical antipsychotics such as risperidone and aripiprazole are also reported to have significant activities against more than nine of the receptors mentioned above. The current research suggests that compounds exhibiting activity against dopamine ($D_2$) and serotonin (5-$HT_{1A}$ and 5-$HT_{2A}$) receptors may have the intended antipsychotic effect (Snyder, S. H., Nature 2008, 452, 38-39; Di Pietro, N. C., Seamans, J. K., Pharmacopsychitry 2007, 40(S1), S27-S33; Stark, A. D. et al., Psychopharmacology 2007, 190, 373-382) while compounds exhibiting activity against other receptors like serotonin, 5$HT_{2C}$, histamine ($H_1$), and adrenergic (alpha 1) may cause adverse side effects such as cardiac arrhythmias.

In addition to poor target selectivity, the most widely used atypical antipsychotics like aripiprazole, risperidone, olanzapine, quetiapine and clozapine are known to undergo cytochrome P450 (CYP 450) mediated hepatic metabolism in the body (Conley, R. R. and Kelly, D. L. Psychopharmacol Bull. 2007, 40(1), 77-97). Hepatic metabolism is also a key determinant of the potential for a given drug to be involved in clinically significant pharmacokinetic drug interactions. Research suggests that aripiprazole is metabolized by CYP 450 isoenzymes 3A4 and 2D6, clozapine and Olanzapine are primarily metabolized by CYP 1A2 and risperidone is metabolized by CYP 2D6. There are significant polymorphisms in patients for CYP isoenzymes and this polymorphism has been shown to substantially increase plasma levels of these atypical antipsychotics. For example, approximately 10% of the Caucasian population lacks CYP2D6 isoenzyme. Patients from the general hospital, geriatric patients, psychogeriatric patients and psychiatric patients are treated more frequently with at least one drug metabolized by CYP2D6 compared to with patients in the general population. Approximately, 50% of psychiatric, psychogeriatric and geriatric patients take at least one drug metabolized by CYP2D6 for other than psychotic indication they have (Mulder H. et al. Ann Pharmacother. 2007, 41(3), 408-13). Thus, poor metabolizers, who lack particular CYP isoenzyme responsible for metabolizing atypical antipsychotic drugs, can be particularly predisposed to adverse drug interactions.

Although, the atypical antipsychotics (aripiprazole, clozapine, risperidone, olanzapine, quetiapine, and ziprasidone) currently in clinical use represent significant advances in treatment of people with schizophrenia, there is a need for new psychotropic drugs with improved safety profiles.

Therefore, development of a novel atypical antipsychotics that preferably undergo significantly non-CYP mediated metabolism in the body and/or have improved therapeutic target selectivity than the currently available therapies would provide effective and safer medicines for the treatment of schizophrenia and related psychotic disorders.

SUMMARY OF THE INVENTION

The present invention provides compounds, synthesis of the compounds, compositions and methods of using the compounds for treating schizophrenia and related psychoses such as acute manic, bipolar disorder, autistic disorder and depression, where the compounds are quinolinone derivatives. The present invention provides methods for synthesizing such quinolinone compounds. The present invention also provides methods for using quinolinone based atypical antipsychotics, and composition of quinolinone based atypical antipsychotics for treating schizophrenia and related psychoses such as acute manic, bipolar disorder, autistic disorder and depression.

The compounds of the subject invention provide next generation novel atypical antipsychotics that are particularly effective and safer for the treatment of schizophrenia. They are advantageous because of their highly desirable metabolic, pharmacokinetics and pharmacological profiles. The compounds of the invention are designed:

1) to exhibit affinity for dopamine $D_2$ receptor;
2) to exhibit affinity for serotonin 5-$HT_{1A}$ and 5-$HT_{2A}$ receptors;
3) to undergo significantly non-oxidative or non-CYP enzyme mediated metabolism in the human body;
4) to metabolize significantly by hydrolytic enzymes such as esterases and/or peptidases in the human body;
5) to form therapeutically inactive or least active metabolite(s).

The features like non-cytochrome P450 enzymes mediated metabolism and therapeutically inactive or least active metabolites in the compounds of subject invention can mitigate the adverse side effects that are derived from drug-drug interactions. Therefore, having these features, the compounds of the inventions are more effective and safer for the treatment of schizophrenia in humans including patients who are on multiple medications for chronic diseases for example: chronic pain, diabetes, cardiovascular diseases, dementia, and asthma, and have poor functioning of liver and kidney.

In one aspect, the present invention provides quinolinone derivatives comprising compounds of structural Formula (I):

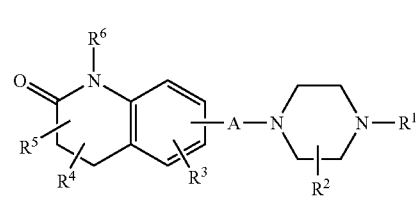

Formula 1 or a pharmaceutically acceptable salt, hydrate or solvate thereof provided that the compound comprises a soft moiety conjugated directly or via a spacer onto or inserted into one of the substituents $R^1$, $R^2$, $R^3$, $R^4$, $R^5$, and $R^6$; wherein 'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$—NH—C(O)—$CH_2$—$CH_2$—, or $(CH_2)_n$—S—C(O)—$CH_2$—$CH_2$—, wherein n is an integer from 1 to 7;

$R^1$, $R^2$, $R^3$, $R^4$, $R^5$ and $R^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide; optionally $R^4$ and $R^5$ may be present on the same carbon; optionally $R^4$ and $R^5$ can together form a 5- or 6-membered ring which may contain one or more heteroatoms selected from O, N, or S and that ring may be optionally substituted with substituents selected from alkyl, substituted alkyl, halo, hydroxyl, and carbonyl.

DETAILED DESCRIPTION OF THE INVENTION

The present invention relates to synthesis, compositions and methods of using quinolinone derivatives which are useful for treating schizophrenia and related psychoses such as acute manic, bipolar disorder, autistic disorder and depression. The present invention provides compounds, compositions and methods for pharmacological treatment of schizophrenia and related psychoses such as acute manic, bipolar disorder, autistic disorder, and depression.

DEFINITIONS

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art. The compositions and formulations described herein can be practiced employing the pharmaceutically acceptable excipients and salts available in *Remington's Pharmaceutical Sciences*, $18^{th}$ Edition (Easton, Pa.: Mack Publishing Company, 1990).

"Compounds of the invention" refers to compounds encompassed by structural Formulae (I)-(X) disclosed herein. The compounds of the invention can be identified either by their chemical structure and/or chemical name. When the chemical structure and chemical name conflict, the chemical structures is determinative of the identity of the compound. The compounds of the invention may contain one or more chiral centers and/or double bonds and therefore, may exist as stereoisomers, such as double-bond isomers (i.e., geometric isomers), enantiomers or diastereoisomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass of conventionally found in nature. Examples of isotopes that may be incorporated into the compounds of the invention include, but are not limited to $^2H$, $^3H$, $^{13}C$, $^{15}N$, $^{18}O$, $^{17}O$, $^{31}P$, $^{32}P$, $^{35}S$, $^{18}F$ and $^{36}Cl$. Further, it should be understood, when partial structures of the compounds of the invention are illustrated, that brackets of dashes indicate the point of attachment of the partial structure to the rest of the molecule.

"Composition of the invention" refers to at least one compound of the invention and a pharmaceutically acceptable vehicle, with which the compound is administered to a patient. When administered to a patient, the compounds of the invention are administered in isolated form, which means separated from a synthetic organic reaction mixture.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to methyl; ethyls such as ethanyl, ethenyl, ethynyl; propyls such as propan-1-yl, propan-2yl, cyclopropan-1-yl, prop-1-en-1-yl, prop-1-en-2-yl, prop-2-en-1-yl (allyl), cycloprop-1-en-1yl, cycloprop-2-en-1yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and like.

The term "alkyl" specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl," are used. Preferably, an alkyl group comprises from 1-20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methy-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien 1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl and the like.

"Acyloxyalkyloxycarbonyl" refers to a radical —C(O)OCR'R"OC(O)R'", where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$OC(O)CH$_3$, —C(O)OCH$_2$OC(O)CH$_2$CH$_3$, —C(O)OCH(CH$_3$)OC(O)CH$_2$CH$_3$, —C(O)OCH(CH$_3$)OC(O)C$_6$H$_5$ and the like.

"Acylalkyloxycarbonyl" refers to a radical —C(O)OCR'R"C(O)R'", where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$C(O)CH$_3$, —C(O)OCH$_2$C(O)CH$_2$CH$_3$, —C(O)OCH(CH$_3$)C(O)CH$_2$CH$_3$, —C(O)OCH(CH$_3$)C(O)C$_6$H$_5$ and the like.

"Acyloxyalkyloxycarbonylamino" refers to a radical —NRC(O)OCR'R"OC(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$OC(O)CH$_3$, —NHC(O)OCH$_2$OC(O)CH$_2$CH$_3$, —NHC(O)OCH(CH$_3$)OC(O)CH$_2$CH$_3$, —NHC(O)OCH(CH$_3$)OC(O)C$_6$H$_5$ and the like.

"Acylalkyloxycarbonylamino" refers to a radical —NRC(O)OCR'R"C(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$C(O)CH$_3$, —NHC(O)OCH$_2$C(O)CH$_2$CH$_3$, —NHC(O)OCH(CH$_3$)C(O)CH$_2$CH$_3$, —NHC(O)OCH(CH$_3$)C(O)C$_6$H$_5$ and the like.

"Acylamino" refers to "Amide" as defined herein.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted by one or more substituents as defined herein. Representative examples include, but are not limited to methoxy, ethoxy, propoxy, butoxy, cyclohexyloxy and the like.

"Alkoxycarbonyl" refers to a radical —C(O)-alkoxy where alkoxy is as defined herein.

"Alkoxycarbonylalkoxy" refers to a radical —OCR'R"C(O)-alkoxy where alkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_3$, —OCH$_2$C(O)OCH$_2$CH$_3$, —OCH(CH$_3$)C(O)OCH$_2$CH$_3$, —OCH(C$_6$H$_5$)C(O)OCH$_2$CH$_3$, —OCH(CH$_2$C$_6$H$_5$)C(O)OCH$_2$CH$_3$, —OC(CH$_3$)(CH$_3$)C(O)OCH$_2$CH$_3$, and the like.

"Alkoxycarbonylalkylamino" refers to a radical —NRCR'R"C(O)-alkoxy where alkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_3$, —N(CH$_3$)CH$_2$C(O)OCH$_2$CH$_3$, —NHCH(CH$_3$)C(O)OCH$_2$CH$_3$, —NHCH(C$_6$H$_5$)C(O)OCH$_2$CH$_3$, —NHCH(CH$_2$C$_6$H$_5$)C(O)OCH$_2$CH$_3$, —NHC(CH$_3$)(CH$_3$)C(O)OCH$_2$CH$_3$, and the like.

"Alkylsulfonyl" refers to a radical —S(O)$_2$R where R is an alkyl, or cycloalkyl group as defined herein that may be optionally substituted by one or more substituents as defined herein. Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined herein that may be optionally substituted by one or more substituents as defined herein. Representative examples include, but are not limited to methylthio, ethylthio, propylthio, butylthio, and the like.

"Amide or Acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, formylamino acetylamino, cyclohexylcarbonylamino, cyclohexylmethylcarbonyl-amino, benzoylamino, benzylcarbonylamino and the like.

"Amino" refers to the radical —NH$_2$

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene, and the like. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or sp$^3$ carbon atom, is replaced with an aryl group. Typically arylalkyl groups include, but not limited to, benzyl, 2-phenylethan-1-yl, 2-phenylethen-1-yl, naphthylmethyl, 2-naphthylethan-1-yl, 2-naphthylethene-1-yl, naphthobenzyl, 2-naphthophenylethan-1-yl and the like. Where specific alkyl moieties are intended, the nomenclature arylalkany, arylalkenyl and/or arylalkynyl is used. Preferably, an arylalkyl group is (C$_6$-C$_{30}$)arylalkyl, e.g., the alkanyl, alkenyl or alkynyl moiety of the arylalkyl group is (C$_1$-C$_{10}$) and the aryl moiety is (C$_6$-C$_{20}$), more preferably, an arylalkyl group is (C$_6$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Arylalkoxy" refers to an —O-arylalkyl radical where arylalkyl is as defined herein that may be optionally substituted by one or more substituents as defined herein.

"Arylalkoxycarbonylalkoxy" refers to a radical —OCR'R"C(O)-arylalkoxy where arylalkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_2$C$_6$H$_5$, —OCH(CH$_3$)C(O)O CH$_2$C$_6$H$_5$, —OCH(C$_6$H$_5$)C(O)O CH$_2$C$_6$H$_5$, —OCH(CH$_2$C$_6$H$_5$)C(O)O CH$_2$C$_6$H$_5$, —OC(CH$_3$)(CH$_3$)C(O)O CH$_2$C$_6$H$_5$, and the like.

"Arylalkoxycarbonylalkylamino" refers to a radical —NRCR'R"C(O)-arylalkoxy where arylalkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_2$C$_6$H$_5$, —N(CH$_3$)CH$_2$C(O)OCH$_2$C$_6$H$_5$, —NHCH(CH$_3$)C(O)OCH$_2$C$_6$H$_5$, —NHCH(C$_6$H$_5$)C(O)OCH$_2$C$_6$H$_5$, —NHCH(CH$_2$C$_6$H$_5$)C(O)OCH$_2$C$_6$H$_5$, —NHC(CH$_3$)(CH$_3$)C(O)OCH$_2$C$_6$H$_5$, and the like.

"Aryloxycarbonyl" refers to radical —C(O)—O-aryl where aryl is defined herein that may be optionally substituted by one or more substituents as defined herein.

"Aryloxycarbonylalkoxy" refers to a radical —OCR'R"C(O)-aryloxy where aryloxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OC$_6$H$_5$, —OCH(CH$_3$)C(O)OC$_6$H$_5$, —OCH(C$_6$H$_5$)C(O)OC$_6$H$_5$, —OCH(CH$_2$C$_6$H$_5$)C(O)OC$_6$H$_5$, —OC(CH$_3$)(CH$_3$)C(O)OC$_6$H$_5$, and the like.

"Aryloxycarbonylalkylamino" refers to a radical —NRCR'R"C(O)-aryloxy where aryloxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OC$_6$H$_5$, —N(CH$_3$)CH$_2$C(O)OC$_6$H$_5$, —NHCH(CH$_3$)C(O)OC$_6$H$_5$, —NHCH(C$_6$H$_5$)C(O)OC$_6$H$_5$, —NHCH(CH$_2$C$_6$H$_5$)C(O)OC$_6$H$_5$, —NHC(CH$_3$)(CH$_3$)C(O)OC$_6$H$_5$, and the like.

"Carbamoyl" refers to the radical —C(O)NRR where each R group is independently, hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methylcarbamate (—NHC(O)OCH$_3$), ethylcarbamate (—NHC(O)OCH$_2$CH$_3$), benzylcarbamate (—NHC(O)OCH$_2$C$_6$H$_5$), and the like.

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methyl carbonate (—C(O)OCH$_3$), cyclohexyl carbonate (—C(O)OC$_6$H$_{11}$), phenyl carbonate (—C(O)OC$_6$H$_5$), benzyl carbonate (—C(O)OCH$_2$C$_6$H$_5$), and the like.

"Carboxy" means the radical —C(O)OH.

"Cyano" means the radical —CN.

"Cycloalkyl" refers to a substituted or unsubstituted cylic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is (C$_3$-C$_{10}$) cycloalkyl, more preferably (C$_3$-C$_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkoxycarbonyl" refers to a radical —C(O)—OR where R is cycloheteroalkyl as defined herein that may be optionally substituted by one or more substituents as defined herein.

"Dialkylamino" means a radical —NRR' where R and R' independently represent an alkyl or cycloalkyl group as defined herein that may be optionally substituted by one or more substituents as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino, and the like.

"Derived from a drug" refers to a fragment that is structurally related to such a drug. The structure of the fragment is identical to the drug except where a hydrogen atom attached to a heteroatom (N or O) has been replaced with a covalent bond to another group (typically, a promoiety). Note that when a drug is a salt form of a carboxylic, phosphonic or phosphoric acid, the corresponding structural fragment derived from such a drug is considered to be derived from the protonated acid form.

"Drug" refers to a compound that exhibits therapeutic and/or prophylactic and/or diagnostic utility when administered in effective amounts to a patient or a mammal.

"Ester" refers to a radical —C(O)OR, where R is alkyl, substituted alkyl, cycloalkyl, substituted cycloalkyl, cycloheteroalkyl, substituted cycloheteroalkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl as defined herein that may be optionally substituted by one or more substituents as defined herein. Representative examples include, but are not limited to, methyl ester (—C(O)OCH$_3$), cyclohexyl ester (—C(O)OC$_6$H$_{11}$), phenyl ester (—C(O)OC$_6$H$_5$), benzyl ester (—C(O)OCH$_2$C$_6$H$_5$), and the like.

"Ether" refers to a radical —OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Halo" means fluoro, chloro, bromo, or iodo.

"Heteroalkoxy" means an —O-heteroalkyl radical where heteroalkyl is as defined herein that may be optionally substituted by one or more substituents as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to —O—, —S—, —O—O—, —S—S—, —OS—, —NR'—, =N—N=, —N=N—, —N=N—NR'—, —PH—, —P(O)₂—, —O—P(O)—, —S(O—, —S(O)₂—, —SnH₂—, and the like, wherein R' is hydrogen, alkyl, substituted alkyl, cycloalkyl, substituted cycloalkyl, aryl or substituted aryl that may be optionally substituted by one or more substituents as defined herein.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined that may be optionally substituted by one or more substituents as defined herein.

"Heteroarylalkyl" refers to an acyclic alkyl radical in which one of the hydrogen atoms bonded to a carbon atom, typically a terminal or sp3 carbon atom, is replaced with a heteroaryl group. Where specific alkyl moieties are intended, the nomenclature heteroarylalkanyl, heteroarylalkenyl and/or heteroarylalkynyl is used. Preferably, the heteroarylalkyl radical is a 6-30 carbon membered heteroarylalkyl, e.g., the alkanyl, alkenyl or alkynyl moiety of the heteroarylalkyl is 1-10 membered and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Hydroxy" means the radical —OH.

"Oxo" means the divalent radical =O.

As used herein, the term "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, laurylsulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Phosphate" refers to a radical —OP(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Phosphonate" refers to a radical —P(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Preventing" or "Prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a group of atoms that when attached to a reactive group in a molecule masks, reduces or prevents that reactivity. Examples of protecting groups can be found in Green et al., "Protective Groups in Organic Chemistry", (Wiley, $2^{nd}$ ed. 1991) and Harrison et al., "Compendium of Synthetic Organic Methods", vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxy-carbonyl ("FMOC"), nitroveratryloxycarbonyl ("NVOC") and the like. Representative hydroxyl protecting groups include, but are not limited to, those where the hydroxyl group is either acylated or alkylated such as benzyl, and trialkylsilyl ethers and allyl ethers.

"Racemate" refers to an equimolar mixture of enantiomers of a chiral molecule.

"Soft moiety" refers to a moiety that contain hydrolyzable bonds that can be incorporated into compounds according to the invention include but not limited are amide (—NHC(O)—), ester (—C(O)O—), carbonate (—OC(O)O—), phosphate (—OP(O)O—), sulfate (—OS(O)(O)O—), carbamate or urethane (—NHC(O)O—), glycoside or other bonds that can be cleaved by hydrolases. A glycoside moiety is formed by the conjugation of a sugar group through its anomeric carbon to another group via oxygen (as an O-glycosidic bond) or sulfur (as a S-glycosidic bond).

"Spacer" refers to a alkyl, aryl, arylalkyl, heteroalkyl and heteroaryl group which is optionally substituted by acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, sulfonamide and/or, in case of alkyl, optionally interrupted by one or more of O, S and N($R^{51}$). $R^{51}$ can be H, lower alkyl, and substituted lower alkyl.

"Substituted" refers to a group in which one or more hydrogen atoms are each independently replaced with the same or different substituents(s). Typical substituents include, but are not limited to, —X, —$R^{54}$, —O⁻, =O, —O$R^{54}$, —S$R^{54}$, —S, =S, —N$R^{54}R^{55}$, =N$R^{54}$, —C$X_3$, —C$F_3$, —CN, —OCN, —SCN, —NO, —N$O_2$, =$N_2$, —$N_3$, S(O)$_2$O⁻, —S(O)$_2$OH, —S(O)$_2$O$R^{54}$, —OS(O)$_2$O$^{31}$, —OS(O)$_2$$R^{54}$, —P(O)(O—)$_2$, —P(O)(O$R^{14}$)(O$^{31}$), —OP(O)(O$R^{54}$)(O$R^{55}$), —C(O)$R^{54}$, —C(S)$R^{54}$, —C(O)O$R^{54}$, —C(O)N$R^{54}R^{55}$, —C(O)O⁻, —C(S)O$R^{54}$, —N$R^{56}$C(O)N$R^{54}R^{55}$, —N$R^{56}$C(S)N$R^{54}R^{55}$, —N$R^{57}$C(N$R^{56}$)N$R^{54}R^{55}$, and —C(N$R^{56}$)N$R^{54}R^{55}$, where each X is independently a halogen; each $R^{54}$, $R^{55}$, $R^{56}$ and $R^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —N$R^{58}R^{59}$, —C(O)$R^{58}$ or —S(O)$_2$$R^{58}$ or optionally $R^{58}$ and $R^{59}$ together with the atom to which they are both attached form a cycloheteroalkyl or substituted cycloheteroalkyl ring; and $R^{58}$ and $R^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR''')-piperazinyl or imidazolyl group wherein said group may be optionally substituted by one or more substituents as defined herein. R''' hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Thioether" refers to a radical —SR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and is severity and the age, weight, etc., of the patient to be treated, and can be determined by one of skill in the art without undue experimentation.

Reference now will be made in detail to preferred embodiments of the invention. While the invention will be described in conjunction with preferred embodiments, it will be understood that it is not intended to limit the invention to those preferred embodiments. To the contrary, it is intended to cover alternatives, modifications, and equivalents as may be included within the spirit and scope of the invention as defined by the appended claims.

COMPOUNDS OF THE INVENTION

The present invention provides quinolinone based antipsychotic agents comprising compounds of structural Formula (I):

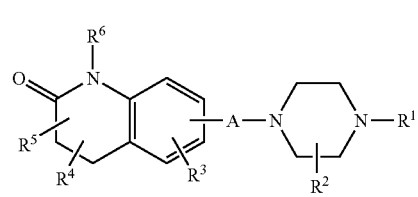

Formula 1 or a pharmaceutically acceptable salt, hydrate or solvate thereof provided that the compounds of the invention comprise a soft moiety conjugated directly or via a spacer onto or inserted into one of the substituents $R^1$, $R^2$, $R^3$, $R^4$, $R^5$, and $R^6$; wherein 'A' is selected to be —O—(C$H_2$)$_n$—, —S—(C$H_2$)$_n$—, —S(O)(O)—(C$H_2$)$_n$—, —NH—(C$H_2$)$_n$—, —C$H_2$—O—(C$H_2$)$_n$—, —(C$H_2$)$_n$—O—C$H_2$—C$H_2$—, —C$H_2$—S—(C$H_2$)$_n$—, —(C$H_2$)$_n$—S—C$H_2$—C$H_2$—, —C$H_2$—S(O)(O)—(C$H_2$)$_n$—, —(C$H_2$)$_n$—S(O)(O)—C$H_2$—C$H_2$—, —O—C(O)—(C$H_2$)$_n$—, —S—C(O)—(C$H_2$)$_n$—, —NH—C(O)—(C$H_2$)$_n$—, —C$H_2$—C(O)—O—(C$H_2$)$_n$—, —C$H_2$—C(O)—NH—(C$H_2$)$_n$—, —C$H_2$—C (O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, CH$_2$)$_n$—S—C(O)—CH$_2$—CH$_2$—, wherein n=1-7;

R$^1$, R$^2$, R$^3$, R$^4$, R$^5$ and R$^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally R$^4$ and R$^5$ may be present on the same carbon; optionally R$^4$ and R$^5$ together form 5- or 6-membered ring which may contain one or more heteroatoms selected from O, N, or S and that ring may be optionally substituted with substituents selected from alkyl, substituted alkyl, halo, hydroxyl, and carbonyl.

In one aspect of the invention, compounds of structural Formula (II) are described:

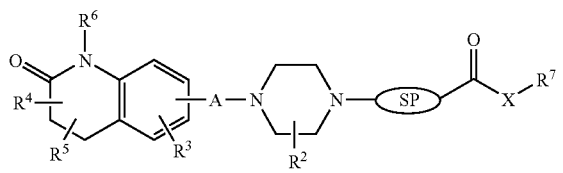

Formula II or a pharmaceutically acceptable salt, hydrate or solvate thereof, wherein X can be O, S, NH or NR$^8$;

SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, CH$_2$)$_n$—S—C(O)—CH$_2$—CH$_2$—, wherein n=1-7;

R$^2$, R$^3$, R$^4$, R$^5$ and R$^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally R$^4$ and R$^5$ may be present on the same carbon; optionally R$^4$ and R$^5$ together form 5- or 6-membered ring which may contain one or more heteroatoms selected from O, N, or S and that ring may be optionally substituted with substituents selected from alkyl, substituted alkyl, halo, hydroxyl, and carbonyl;

R$^7$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; R$^7$ and R$^8$ together form 5- or 6-membered ring which optionally may contain one or more heteroatoms selected from O, N, or S and that may be optionally substituted with one or more substituents selected from alkyl, halo, hydroxyl, carbonyl; or together with R$^8$ forms 5- or 6-membered lactones and lactams that may be optionally substituted with one or more substituents selected from alkyl, halo, hydroxyl or carbonyl;

R$^8$ is selected to be alkyl, substituted alkyl or R$^7$ and R$^8$ together form 5- or 6-membered ring which optionally may contain one or more heteroatoms selected from O, N, or S and that may be optionally substituted with one or more substituents selected from alkyl, halo, hydroxyl, carbonyl; or together with R$^7$ forms 5- or 6-membered lactones and lactams that may be optionally substituted with one or more substituents selected from alkyl, halo, hydroxyl and carbonyl.

In another aspect of the invention, compounds comprise structural Formula (III):

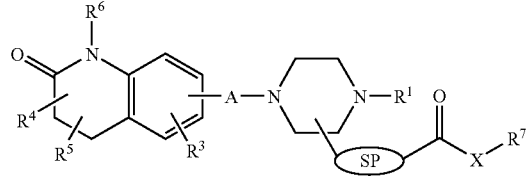

Formula III or a pharmaceutically acceptable salt, hydrate or solvate thereof, wherein X can be O, S, NH or NR$^8$;

SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$ —NH—C(O)—CH$_2$—CH$_2$—, CH$_2$)$_n$—S—C(O)—CH$_2$—CH$_2$—, wherein n=1-7;

$R^1$, $R^3$, $R^4$, $R^5$ and $R^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally $R^4$ and $R^5$ may be present on the same carbon; optionally $R^4$ and $R^5$ together form 5- or 6-membered ring which may contain one or more heteroatoms selected from O, N, or S and that ring may be optionally substituted with substituents selected from alkyl, substituted alkyl, halo, hydroxyl, and carbonyl;

$R^7$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; $R^7$ and $R^8$ together form 5- or 6-membered ring which optionally may contain one or more heteroatoms selected from O, N, or S and that may be optionally substituted with one or more substituents selected from alkyl, halo, hydroxyl, carbonyl; or together with $R^8$ forms 5- or 6-membered lactones and lactams that may be optionally substituted with one or more substituents selected from alkyl, halo, hydroxyl or carbonyl;

$R^8$ is selected to be alkyl, substituted alkyl or $R^7$ and $R^8$ together form 5- or 6-membered ring which optionally may contain one or more heteroatoms selected from O, N, or S and that may be optionally substituted with one or more substituents selected from alkyl, halo, hydroxyl, carbonyl; or together with $R^7$ forms 5- or 6-membered lactones and lactams that may be optionally substituted with one or more substituents selected from alkyl, halo, hydroxyl and carbonyl.

In another aspect of the invention, compounds comprise structural Formula (IV):

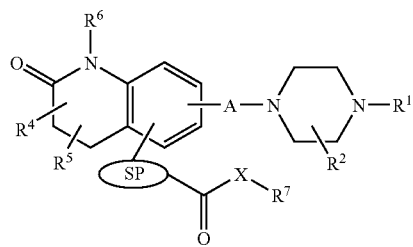

Formula IV or a pharmaceutically acceptable salt, hydrate or solvate thereof, wherein X can be O, S, NH or NR$^8$;
SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$, —NH—C(O)—CH$_2$—CH$_2$—, CH$_2$)$_n$—S—C(O)—CH$_2$—CH$_2$—, wherein n=1-7;

$R^1$, $R^2$, $R^4$, $R^5$, and $R^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally $R^4$ and $R^5$ may be present on the same carbon; optionally $R^4$ and $R^5$ together form 5- or 6-membered ring which may contain one or more heteroatoms selected from O, N, or S and that ring may be optionally substituted with substituents selected from alkyl, substituted alkyl, halo, hydroxyl, and carbonyl;

$R^7$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; $R^7$ and $R^8$ together form 5- or 6-membered ring which optionally may contain one or more heteroatoms selected from O, N, or S and that may be optionally substituted with one or more substituents selected from alkyl, halo, hydroxyl, carbonyl; or together with $R^8$ forms 5- or 6-membered lactones and lactams that may be optionally substituted with one or more substituents selected from alkyl, halo, hydroxyl or carbonyl;

$R^8$ is selected to be alkyl, substituted alkyl or $R^7$ and $R^8$ together form 5- or 6-membered ring which optionally may contain one or more heteroatoms selected from O, N, or S and that may be optionally substituted with one or more substituents selected from alkyl, halo, hydroxyl, carbonyl; or together with $R^7$ forms 5- or 6-membered lactones and lactams that may be optionally substituted with one or more substituents selected from alkyl, halo, hydroxyl and carbonyl.

In another aspect of the invention, compounds comprise structural Formula (V):

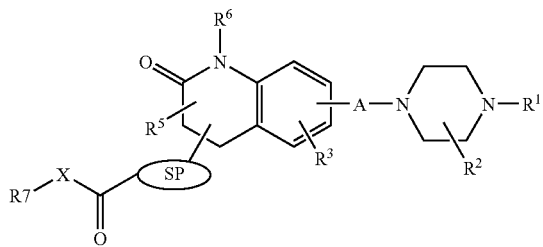

Formula V or a pharmaceutically acceptable salt, hydrate or solvate thereof; wherein X can be O, S, NH or $NR^8$;

SP is a spacer;

'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$ —NH—C(O)—$CH_2$—$CH_2$—, $CH_2)_n$—S—C(O)—$CH_2$—$CH_2$—, wherein n=1-7;

$R^1$, $R^2$, $R^3$, $R^5$ and $R^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally $R^4$ and $R^5$ may be present on the same carbon;

$R^7$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; $R^7$ and $R^8$ together form 5- or 6-membered ring which optionally may contain one or more heteroatoms selected from O, N, or S and that may be optionally substituted with one or more substituents selected from alkyl, halo, hydroxyl, carbonyl; or together with $R^8$ forms 5- or 6-membered lactones and lactams that may be optionally substituted with one or more substituents selected from alkyl, halo, hydroxyl or carbonyl;

$R^8$ is selected to be alkyl, substituted alkyl or $R^7$ and $R^8$ together form 5- or 6-membered ring which optionally may contain one or more heteroatoms selected from O, N, or S and that may be optionally substituted with one or more substituents selected from alkyl, halo, hydroxyl, carbonyl; or together with $R^7$ forms 5- or 6-membered lactones and lactams that may be optionally substituted with one or more substituents selected from alkyl, halo, hydroxyl and carbonyl.

In another aspect of the invention, compounds comprise structural Formula (VI):

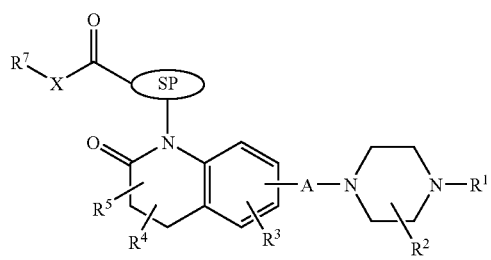

Formula VI or a pharmaceutically acceptable salt, hydrate or solvate thereof; wherein X can be O, S, NH or $NR^8$;

SP is a spacer;

'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$ —NH—C(O)—$CH_2$—$CH_2$—, $CH_2)_n$—S—C(O)—$CH_2$—$CH_2$—, wherein n=1-7;

$R^1$, $R^2$, $R^3$, $R^4$ and $R^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally $R^4$ and $R^5$ may be present on the same carbon; optionally $R^4$ and $R^5$ together form 5- or 6-membered ring which may contain one or more heteroatoms selected from O, N, or S and that ring may be optionally substituted with substituents selected from alkyl, substituted alkyl, halo, hydroxyl, and carbonyl;

$R^7$ is selected to be alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; $R^7$ and $R^8$ together form 5- or 6-membered ring which optionally may contain one or more heteroatoms selected from O, N, or S and that may be optionally substituted with one or more substituents selected from alkyl, halo, hydroxyl, carbonyl; or together with $R^8$ forms 5- or 6-membered lactones and lactams that may be optionally substituted with one or more substituents selected from alkyl, halo, hydroxyl or carbonyl;

$R^8$ is selected to be alkyl, substituted alkyl or $R^7$ and $R^8$ together form 5- or 6-membered ring which optionally may contain one or more heteroatoms selected from O, N, or S and that may be optionally substituted with one or more substituents selected from alkyl, halo, hydroxyl, carbonyl; or together with $R^7$ forms 5- or 6-membered lactones and lactams that may be optionally substituted with one or more substituents selected from alkyl, halo, hydroxyl and carbonyl.

In another aspect of the invention, compounds comprise structural Formula (VII):

Formula VII

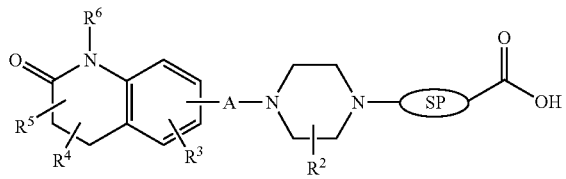

or a pharmaceutically acceptable salt, hydrate or solvate thereof; wherein

SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, —(CH$_2$)$_n$—NH—C(O)—CH$_2$—CH$_2$—, —(CH$_2$)$_n$—S—C(O)—CH$_2$—CH$_2$—, wherein n=1-7;

$R^2$, $R^3$, $R^4$, $R^5$ and $R^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally $R^4$ and $R^5$ may be present on the same carbon; optionally $R^4$ and $R^5$ together form 5- or 6-membered ring which may contain one or more heteroatoms selected from O, N, or S and that ring may be optionally substituted with substituents selected from alkyl, substituted alkyl, halo, hydroxyl, and carbonyl.

In another aspect of the invention, compounds comprise structural Formula (VIII):

Formula VIII

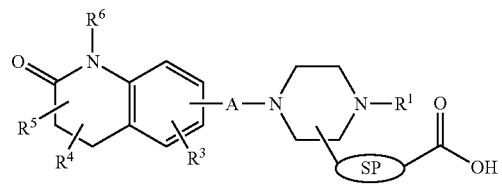

or a pharmaceutically acceptable salt, hydrate or solvate thereof, wherein

SP is a spacer;

'A' is selected to be —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, —(CH$_2$)$_n$—NH—C(O)—CH$_2$—CH$_2$—, —(CH$_2$)$_n$—S—C(O)—CH$_2$—CH$_2$—, wherein n=1-7;

$R^1$, $R^3$, $R^4$, $R^5$ and $R^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally $R^4$ and $R^5$ may be present on the same carbon; optionally $R^4$ and $R^5$ together form 5- or 6-membered ring which may contain one or more heteroatoms selected from O, N, or S and that ring may be optionally substituted with substituents selected from alkyl, substituted alkyl, halo, hydroxyl, and carbonyl.

In another aspect of the invention, compounds comprise structural Formula (IX):

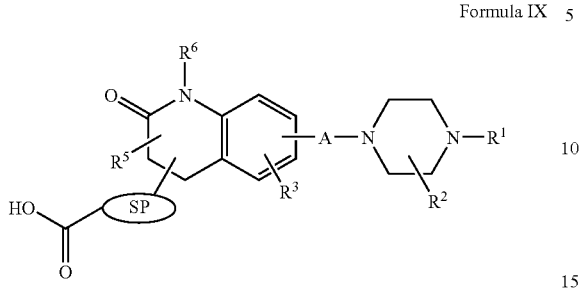

Formula IX or a pharmaceutically acceptable salt, hydrate or solvate thereof; wherein X can be O, S, NH or $NR^8$;
SP is a spacer;
'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$—NH—C(O)—$CH_2$—$CH_2$—, $CH_2)_n$—S—C(O)—$CH_2$—$CH_2$—, wherein n=1-7;
$R^1$, $R^2$, $R^3$, $R^5$ and $R^6$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally $R^4$ and $R^5$ may be present on the same carbon; optionally $R^4$ and $R^5$ together form 5- or 6-membered ring which may contain one or more heteroatoms selected from O, N, or S and that ring may be optionally substituted with substituents selected from alkyl, substituted alkyl, halo, hydroxyl, and carbonyl.

In another aspect of the invention, compounds comprise structural Formula (X):

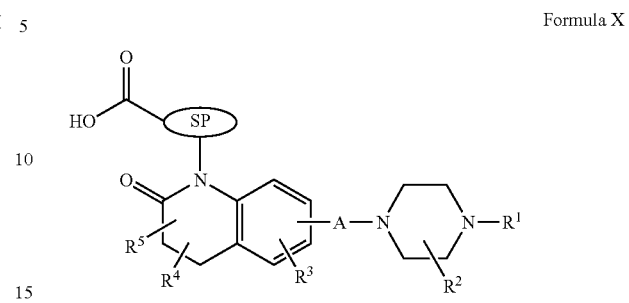

Formula X or a pharmaceutically acceptable salt, hydrate or solvate thereof, wherein
SP is a spacer;
'A' is selected to be —O—$(CH_2)_n$—, —S—$(CH_2)_n$—, —S(O)(O)—$(CH_2)_n$—, —NH—$(CH_2)_n$—, —$CH_2$—O—$(CH_2)_n$—, —$(CH_2)_n$—O—$CH_2$—$CH_2$—, —$CH_2$—S—$(CH_2)_n$—, —$(CH_2)_n$—S—$CH_2$—$CH_2$—, —$CH_2$—S(O)(O)—$(CH_2)_n$—, —$(CH_2)_n$—S(O)(O)—$CH_2$—$CH_2$—, —O—C(O)—$(CH_2)_n$—, —S—C(O)—$(CH_2)_n$—, —NH—C(O)—$(CH_2)_n$—, —$CH_2$—C(O)—O—$(CH_2)_n$—, —$CH_2$—C(O)—NH—$(CH_2)_n$—, —$CH_2$—C(O)—S—$(CH_2)_n$—, —$(CH_2)_n$—C(O)—O—$CH_2$—$CH_2$—, —$(CH_2)_n$—C(O)—NH—$CH_2$—$CH_2$—, —$(CH_2)_n$—C(O)—S—$CH_2$—$CH_2$—, —$CH_2$—O—C(O)—$(CH_2)_n$—, —$CH_2$—NH—C(O)—$(CH_2)_n$—, —$CH_2$—S—C(O)—$(CH_2)_n$—, —$(CH_2)_n$—O—C(O)—$CH_2$—$CH_2$—, $(CH_2)_n$—NH—C(O)—$CH_2$—$CH_2$—, $CH_2)_n$—S—C(O)—$CH_2$—$CH_2$—, wherein n=1-7;
$R^1$, $R^2$, $R^3$, $R^4$ and $R^5$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, and sulfonamide; optionally $R^4$ and $R^5$ may be present on the same carbon; optionally $R^4$ and $R^5$ together form 5- or 6-membered ring which may contain one or more heteroatoms selected from O, N, or S and that ring may be optionally substituted with substituents selected from alkyl, substituted alkyl, halo, hydroxyl, and carbonyl.

The compounds of this invention described herein can have one or more of the following characteristics or properties:

(a) Compounds of the invention can have affinity for dopamine $D_2$ receptors;

(b) Compounds of the invention can have affinity for serotonin 5-$HT_{1A}$ receptors;

(c) Compounds of the invention can have affinity for serotonin 5-$HT_{2A}$ receptors;

(d) Compounds according to the invention contain at least one hydrolyzable bond that can be cleaved non-oxidatively by hydrolytic enzyme(s);

(e) The primary metabolites of compounds result from a non-oxidative metabolic pathway;

(f) The primary metabolite(s), regardless of the electrophysiological properties of the parent drug, has, or have, negligible inhibitory activity at the HERG (human ether-a-go-go related gene) potassium channel at the normal therapeutic concentration of the parent drug in plasma (e.g. the concentration of the metabolite must be at least five times higher than the normal therapeutic concentration of the parent compound before activity at the HERG potassium channel is observed);

(g) Compounds of the invention, as well as the metabolites thereof, do not cause, or have reduced incidence of metabolic drug-drug interaction (DDI) when co-administered with other drugs;

(h) Compounds of the invention, as well as metabolites thereof, do not substantially elevate liver function test (LFT) values when administered alone;

(i) Oral bioavailability of the compounds is consistent with oral administration using standard pharmacological oral formulations; however, the compounds, and compositions thereof, can also be administered using any delivery system that produces constant and controllable blood levels overt time.

In one aspect, the invention provides compounds having any two or more of the above identified characteristics or properties. In another aspect, the invention provides for compounds having at least any three or more of the above identified properties or characteristics. In yet another aspect, the compounds, and compositions thereof, have any combination of four to seven of the above identified characteristics or properties. Preferably, the compounds of the invention have all nine characteristics or properties.

Preferably, the primary metabolite(s) of the inventive compounds, regardless of the electrophysiological properties of the parent drug, has, or have, negligible inhibitory activity at the HERG potassium channel at normal therapeutic concentrations of the drug in plasma. In other words, the concentration of the metabolite can be at least five times higher than the normal therapeutic concentration of the parent compound before activity at the HERG potassium channel is observed. Preferably, the concentration of the metabolite can be at least ten times higher than the normal therapeutic concentration of the parent compound before activity at the HERG potassium channel is observed.

Compounds according to the invention are primarily metabolized by endogenous hydrolytic enzymes via hydrolyzable bonds engineered into their structures. The primary metabolites resulting from this metabolic pathway are water soluble and do not have, or show a reduced incidence of, DDI when administered with other medications (drugs). Non-limiting examples of hydrolyzable bonds that can be incorporated into compounds according to the invention include amide, ester, carbamate, carbonate, phosphate, sulfate, urea, glycoside, or other bonds that can be cleaved by hydrolases.

Additional modifications of the compounds disclosed herein can readily be made by those skilled in the art. Thus, analogs and salts of the exemplified compounds are within the scope of the subject invention. With knowledge of the compounds of the subject invention skilled artisans can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitution at certain locations in the compound.

The subject invention further pertains to enantiomerically isolated compounds, and compositions comprising the compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. Thus, for example, the compounds are at least about 90% enantiomeric excess, preferably at least about 95% enantiomeric excess, more preferably at least about 97% enantiomeric excess., or even more preferably, at least 99% or greater than 99% enantiomeric excess.

Synthesis of the Compounds of the Invention

The compounds of the invention can be obtained via the synthetic methods illustrated in Schemes 1-9. Those of skill in the art will appreciate that a preferred synthetic route to the compounds of the invention will consist of attaching or incorporating soft-moieties to quinolinone derivatives of Formulae (I)-(X). Several methods have been described in the art for the synthesis of quinolinone derivatives (see, e.g. Rajendran, C. et al. WO 2006/038220, Chava, S. et al., WO 2006/030446, Paul, S, et al., WO 2004/099152, Oshiro, Y. et al., *J. Med. Chem.* 1998, 41, 658-667). Other methods are known in the art for synthesizing indanone, which are readily accessible to the skilled artisan. The soft-moieties attached to spacers thereof are commercially available or can be prepared by established procedures (See e.g., Green et al., "Protective Groups in Organic Chemistry," (Wiley, 4th ed., 2006); Harrison et al "Compendium of Synthetic Organic Methods," vols. 1-8 (John Wiley and Sons, 1971-1996); "Beilstein Handbook of Organic Chemistry, Frankfurt, Germany; Feiser et al, "Reagents for Organic Synthesis," Volumes 1-45, Karger, 1991; March, Advanced Organic Chemistry," Wiley Interscience, $4^{th}$ ed., 1991; Larock "Comprehensive Organic Transformations," Wiley-VCH Publishers, $2^{nd}$ ed., 1999; Paquette, "Encyclopedia of Reagents for Organic Synthesis," John Wiley and Sons, $1^{st}$ ed., 1995).

Accordingly, starting materials useful for preparing compounds of the invention and intermediates thereof are commercially available or can be prepared by well-known synthetic methods. Other methods for the synthesis of quinolinones described herein are either described in the art or will be readily apparent to the skilled artisan in view of the references provided above and may be used to synthesize the compounds of the invention. Accordingly, the methods presented in the Schemes herein are illustrative rather than comprehensive.

In one method selected quinolinone derivatives comprising Formulae (I)-(X) were prepared as described in Scheme 1. The starting building block 7-(hydroxyl)-3,4-dihydroquinolin-2(1H)-one (1) was purchased from Sigma-Aldrich. The quinolinone 1 was treated with 1,4-dibromobutane in the presence of a mild base potassium carbonate ($K_2CO_3$) in anhydrous N,N-dimethylformamide (DMF) at around 70° C. to give the corresponding alkylated quinolinone 3 in over 70% yield. The quinolinone 3 was reacted with commercially available (purchased from Sigma-Aldrich) 1-(2-methoxyphenyl)piperazine hydrochloride 4 in presence of diisopropylethylamine (DIEA) in acetonitrile at around 60° C. for 12 h to give the quinolinone 5 in good yield. The treatment of methoxyphenyl substituted quinolinone 5 with aluminum chloride in presence of ethanethiol in dichloromethane (DCM) afforded the corresponding quinolinone 6. The resulting quinolinone was further treated with an appropriate alkylhalide carrying terminal ester group 7 under standard alkylating conditions using cesium carbonate in DMF at around 70° C. to give the corresponding quinolinone carrying an ester group 8 in nearly quantitative yield. The alkyl halides carrying terminal ester group comprising general structure 7 were either purchased from commercial sources or prepared by well known methods available in the literature. Five examples of alkyl halides with terminal ester groups 7a-e are given in Scheme 1. The hydrochloride salt 9 of quinolinone 8 was prepared by treating it with 2M ethereal solution of hydrogen chloride (HCl) in DCM at room temperature in excellent yield.

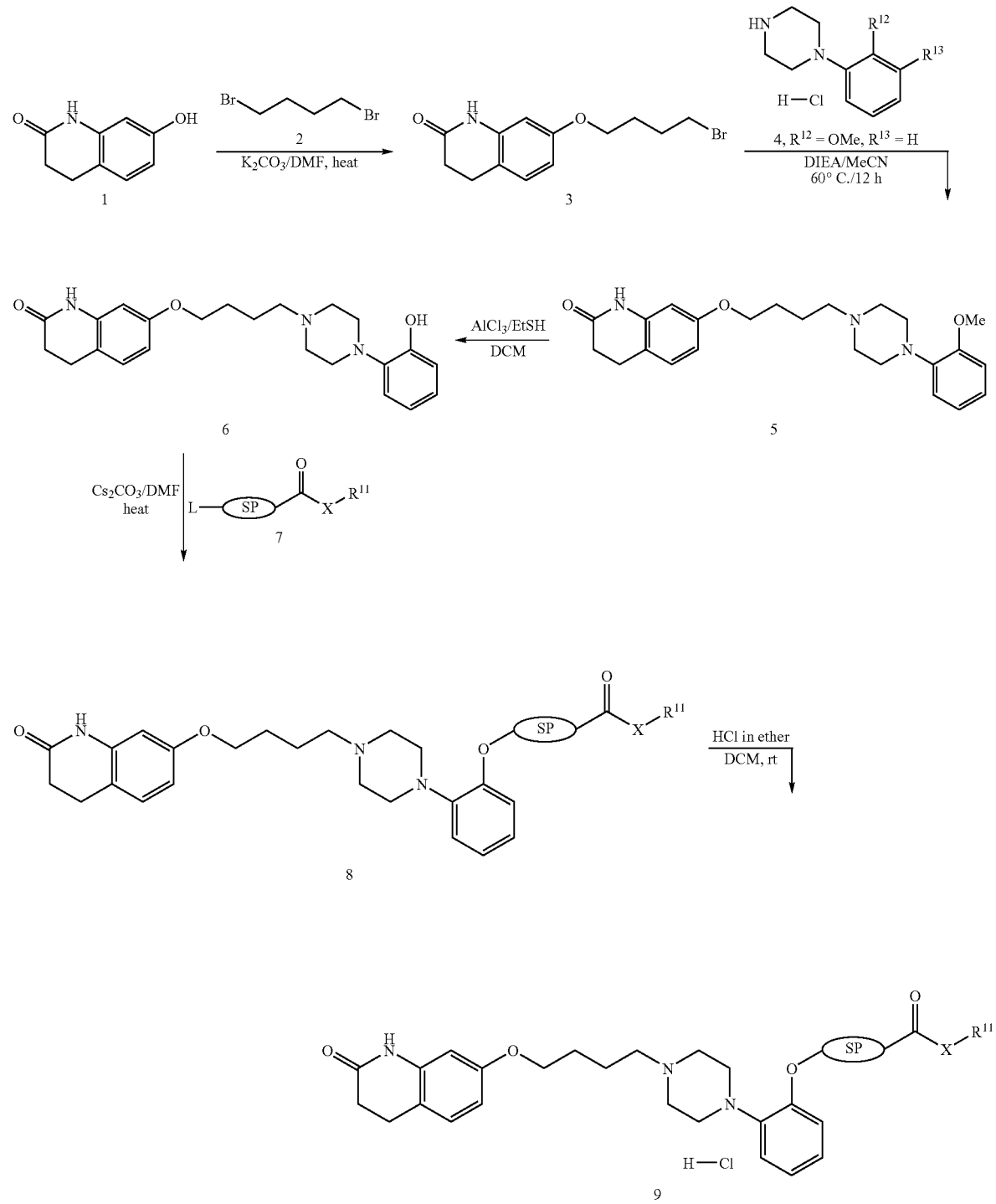

L = Cl, Br and X = O, NH

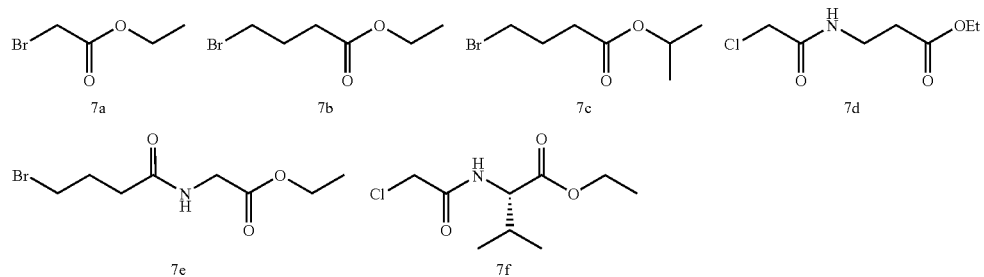

7a, 7b, 7c, 7d, 7e, 7f

In another method selected quinolinone derivatives comprising Formulae (I)-(X) were prepared as described in Scheme 2. The starting 2-hydroxyphenyl substituted piperazine 10 was purchased from Sigma-Aldrich. The N—BOC protected piperazine 12 was prepared by treating piperazine 10 with di-tert-butylcarbonate (BOC) in tetrahydrofuran (THF) at 60° C. for 6 h in over 92% yield. The N—BOC protected piperazine was alkylated with an appropriate alkyl halide carrying a terminal ester group 7 as described for the synthesis of quinolinone 8 as illustrated in Scheme 1 to give the corresponding piperazine 13 in good yield. The BOC group was removed under standard conditions by treating with a solution of trifluoroacetic acid (TFA) in DCM at room temperature in quantitative yield. The resulting free base intermediate was then treated with bromoalkoxy-quinolinone 3 in presence of DIEA in acetonitrile at about 60° C. to give the quinolinone derivative 14 in good yield. The quinolinone 14 was treated with HCl in DCM to give the corresponding hydrochloride salt 15.

Scheme 2

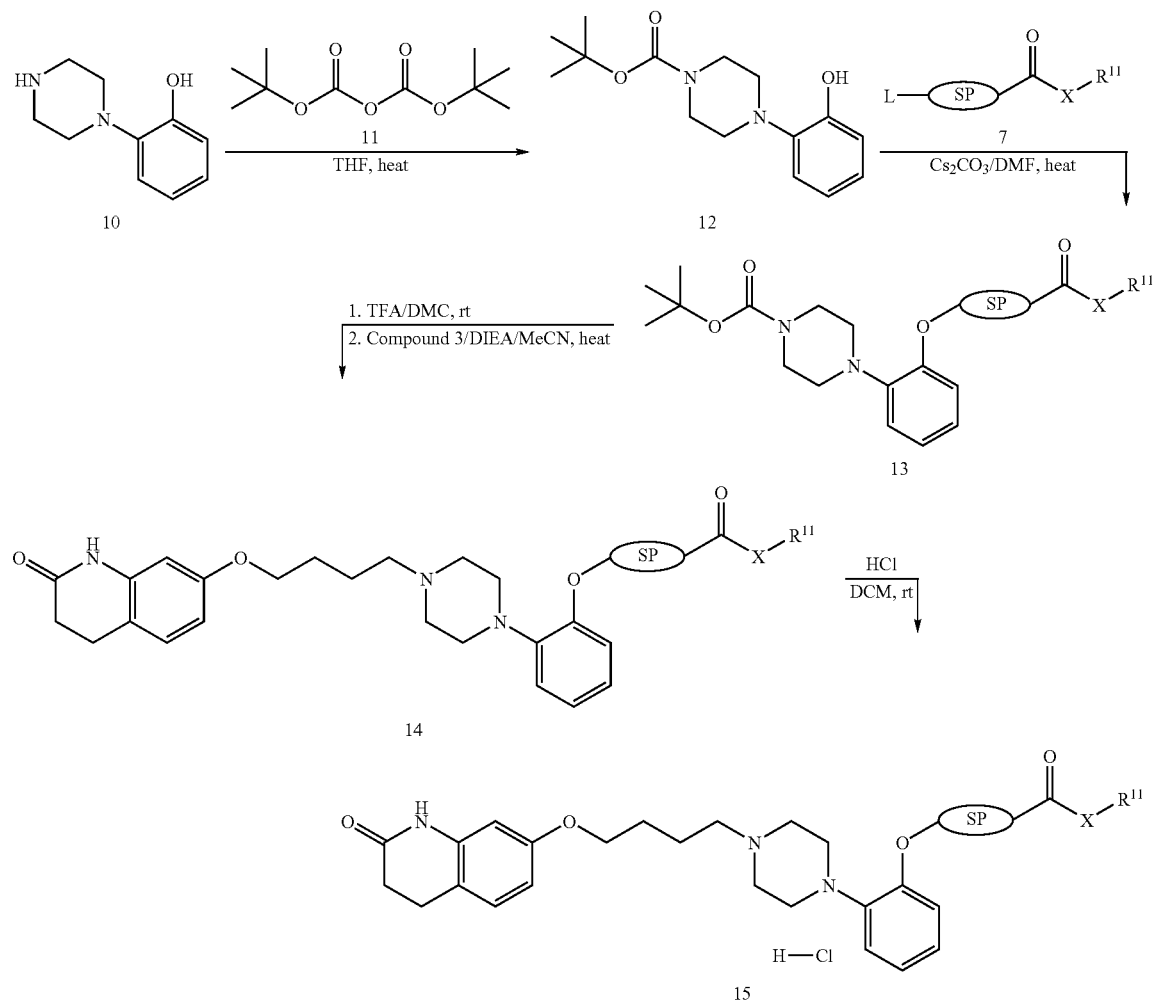

L = Cl, Br and X = O, NH

In another method selected quinolinone derivatives comprising Formulae (I)-(X) were prepared as described in Scheme 3. The suitable N-phenyl substituted piperazine 4 was alkylated with appropriate bromoalkyl carboxylic acid esters 16 in presence of DIEA in acetonitrile at about 60° C. to give the corresponding carboxylic acid ester derivative 17. The saponification of the ester 17 under standard conditions as illustrated in Scheme 3 afforded the corresponding carboxylic acid 18 in nearly quantitative yield. The carboxylic acid 18 was coupled with 7-hydroxyquninolinone 1 under standard ester or peptide bond formation conditions using N,N-dicyclohexylcarbodiimide (DCC) in presence of base N,N-dimethylaminopyridine (DMAP) in DCM to yield the corresponding quinolinone 19 in good yield. The quinolinone 19 was treated with HCl in DCM to form its hydrochloride salt 20.

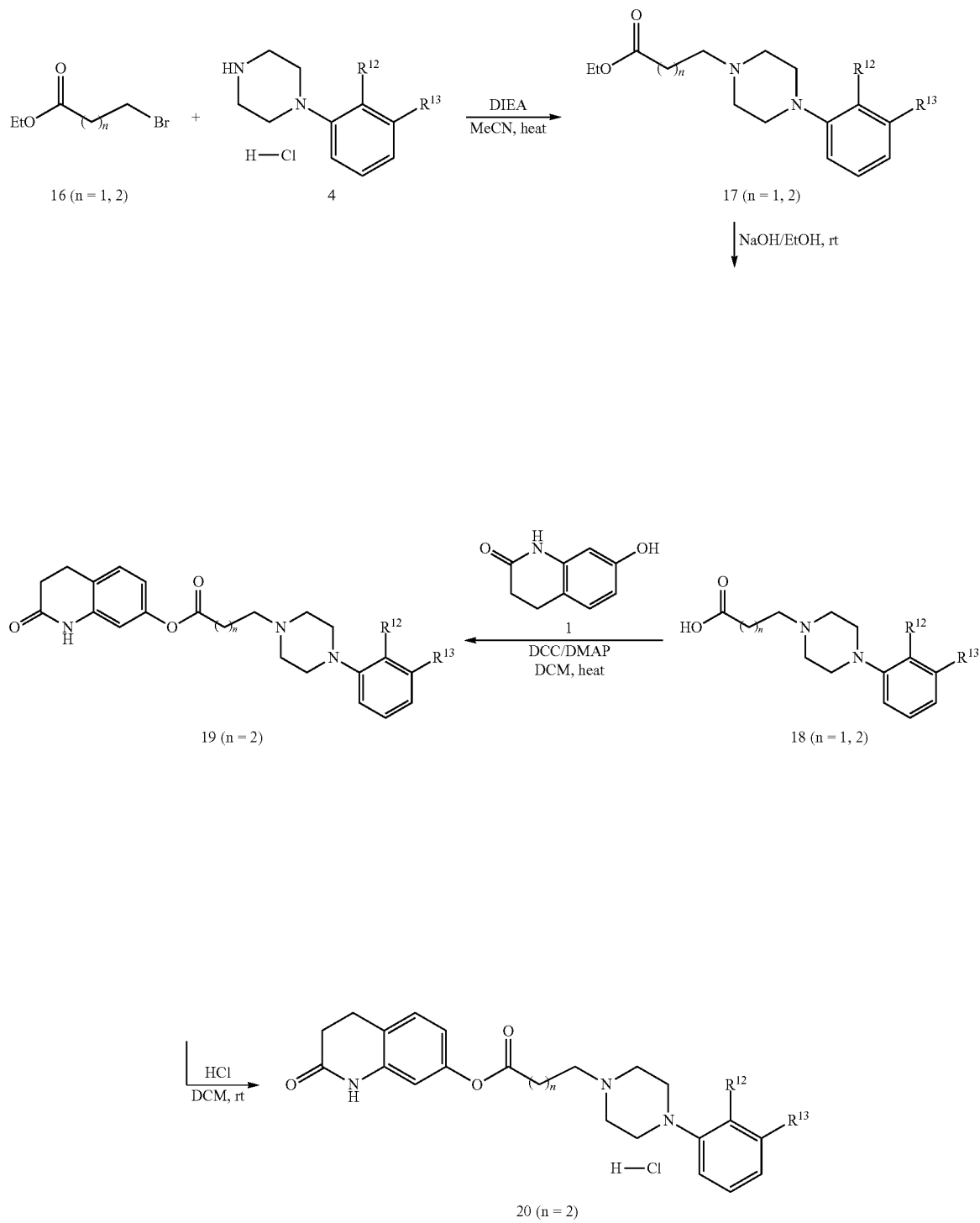

Scheme 3

In another method selected quinoline derivatives comprising Formulae (I)-(X) were prepared as described in Scheme 4. The suitable piperazine derivative 17 carrying ester function group was subjected to standard reduction conditions using sodium borohydride (NaBH₄) in ethanol (EtOH) at reflux temperature to give the carbinol 21 in good yield. The carbinol 21 was coupled with carboxylic acid 22 under standard coupling conditions using DCC in presence of DMAP in THF at room temperature to form the corresponding quinolinone 23 in good yield. The quinolinone 23 was treated with HCl to form its HCl salt 24 in good yield.

Scheme 4

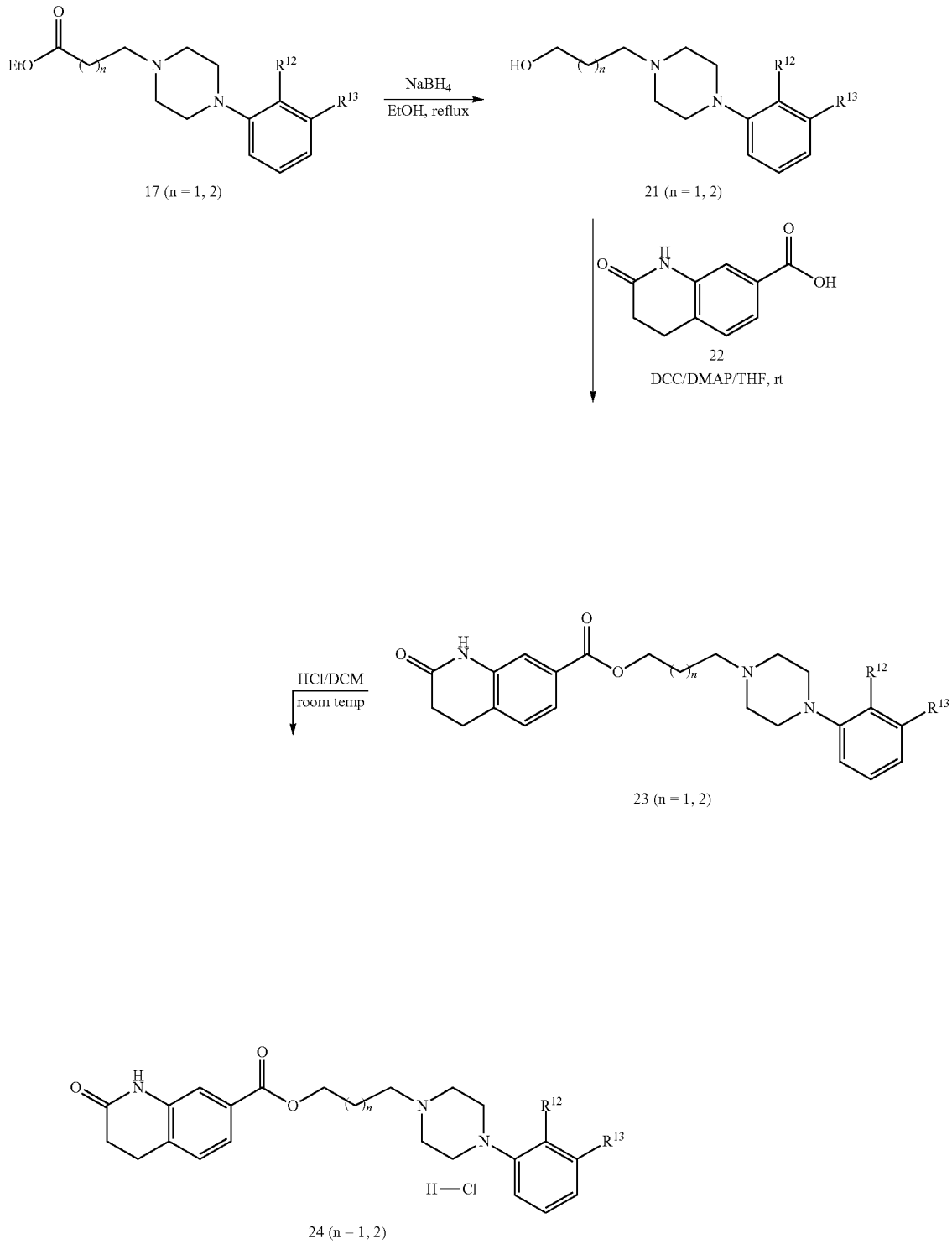

In another method selected quinoline derivatives comprising Formulae (I)-(X) were prepared as described in Scheme 5. An appropriate N—BOC protected piperazine derivative 13 (Scheme 2) was treated with trifluoroacetic acid in DCM at room temperature to give the corresponding piperazine derivative 25 in nearly quantitative yield. The piperazine 25 was alkylated with 3-bromopropanol 26 in presence of a base DIEA in acetonitrile at about 60° C. to afford the carbinol 27 which after coupling with quinolinone 22 as described for the synthesis of quinolinone 23 as illustrated in Scheme 4 gave the corresponding quinolinone ester 28 in good yield.

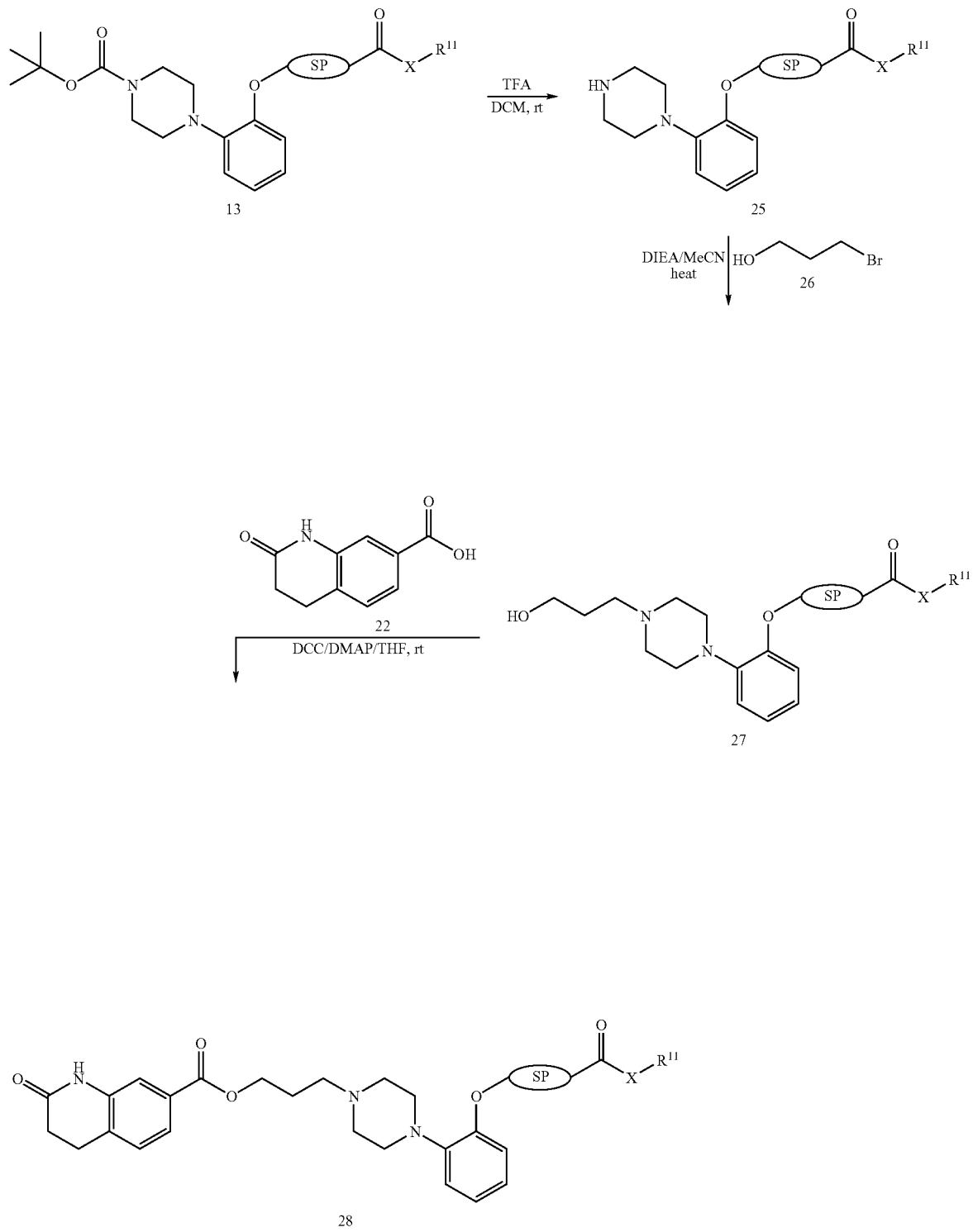

In another method selected quinoline derivatives comprising Formulae (I)-(X) were prepared as described in Scheme 6. The quinolinone 35 was synthesized in 6 synthetic steps starting from beta-alanine ethyl ester hydrochloride 29. The aminoacid ester 29 was protected with tert-butoxycarbonyl moiety using di-tert-butyloxycarbonyl under standard conditions to give the N—BOC derivative 30. The compound 30 gave the carbinol 31 after subjecting it to standard reduction conditions using sodium borohydride in ethanol in good yield. The carbinol 31 was reacted with p-toluene sulfonyl- chloride in presence of a base pyridine in DCM to afford the corresponding tosylate 32 in good yield. The tosylate 32 was treated with substituted piperazine 4 in DIEA in N,N-dimethylformamide (DMF) to give the piperazine derivative 33 in good yield. The BOC protecting group on the piperazine derivative 33 was cleaved off using TFA in DCM to yield the amine 34 which was coupled with quinolinone carboxylic acid 22 under standard reaction conditions to yield the quinolinone amide derivative 35.

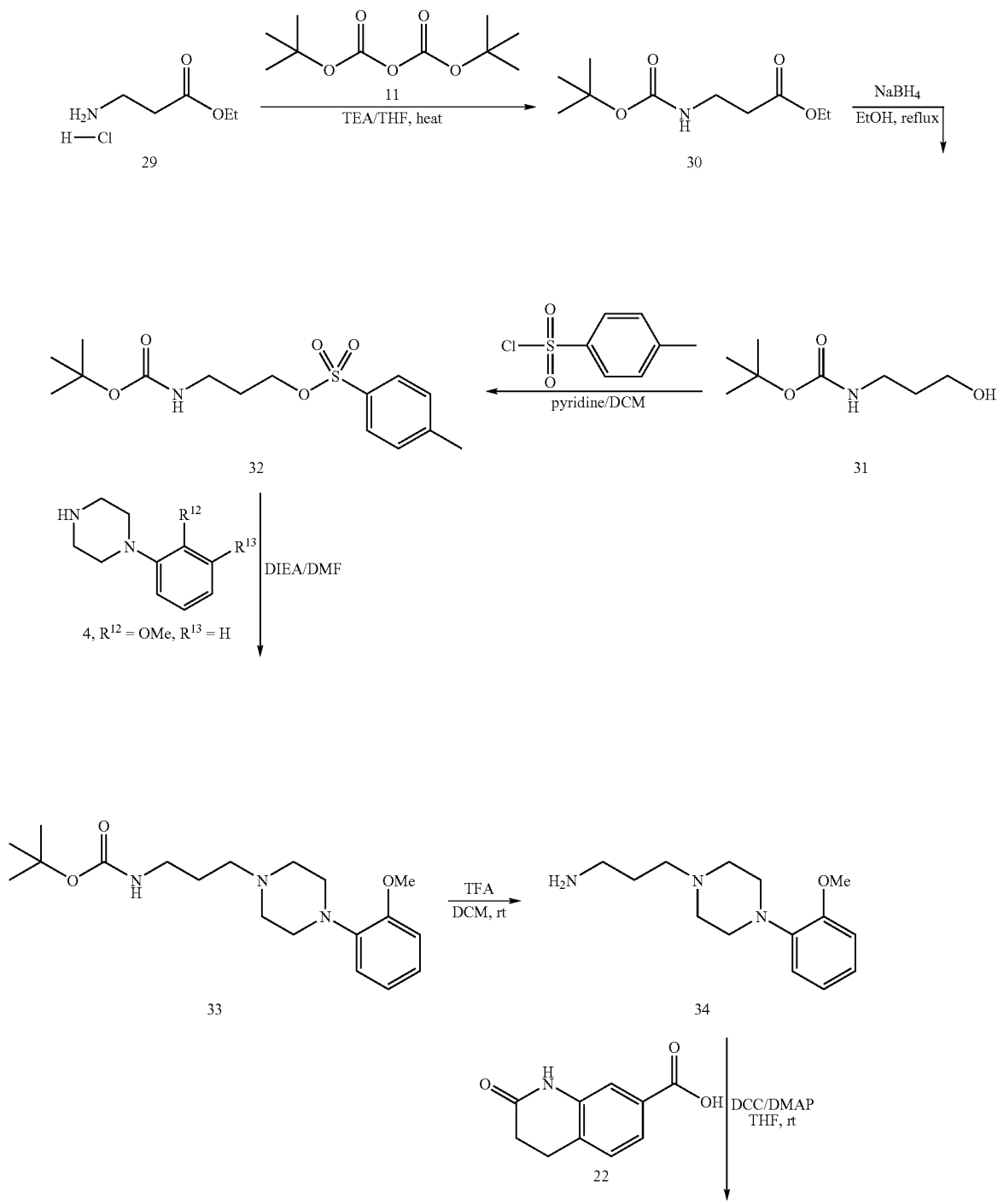

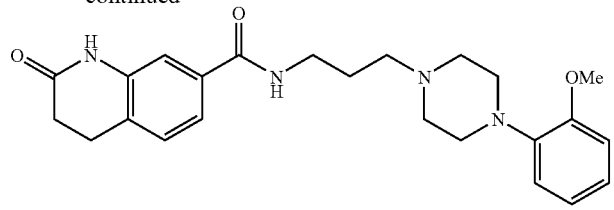

35

In another method selected quinolinone derivatives comprising Formulae (I)-(X) were prepared as described in Scheme 7. The quinolinonecarboxylic acid 22 was converted into its ethyl ester 36 under standard esterification conditions using ethanol and catalytic amounts of concentrated sulfuric acid in good yield. The quinolinone ester 36 was subjected to standard reduction conditions using sodium borohydride (NaBH$_4$) in ethanol to give the carbinol 37. The carbinol 37 was coupled with an appropriate piperazine derivative 18 carrying a carboxylic acid moiety under standard coupling conditions using DCC in presence of DMAP in THF to afford the corresponding quinolinone 38 in good yield. The quinolinone 38 was further treated with HCl in DCM to form its hydrochloride salt 39.

Scheme 7

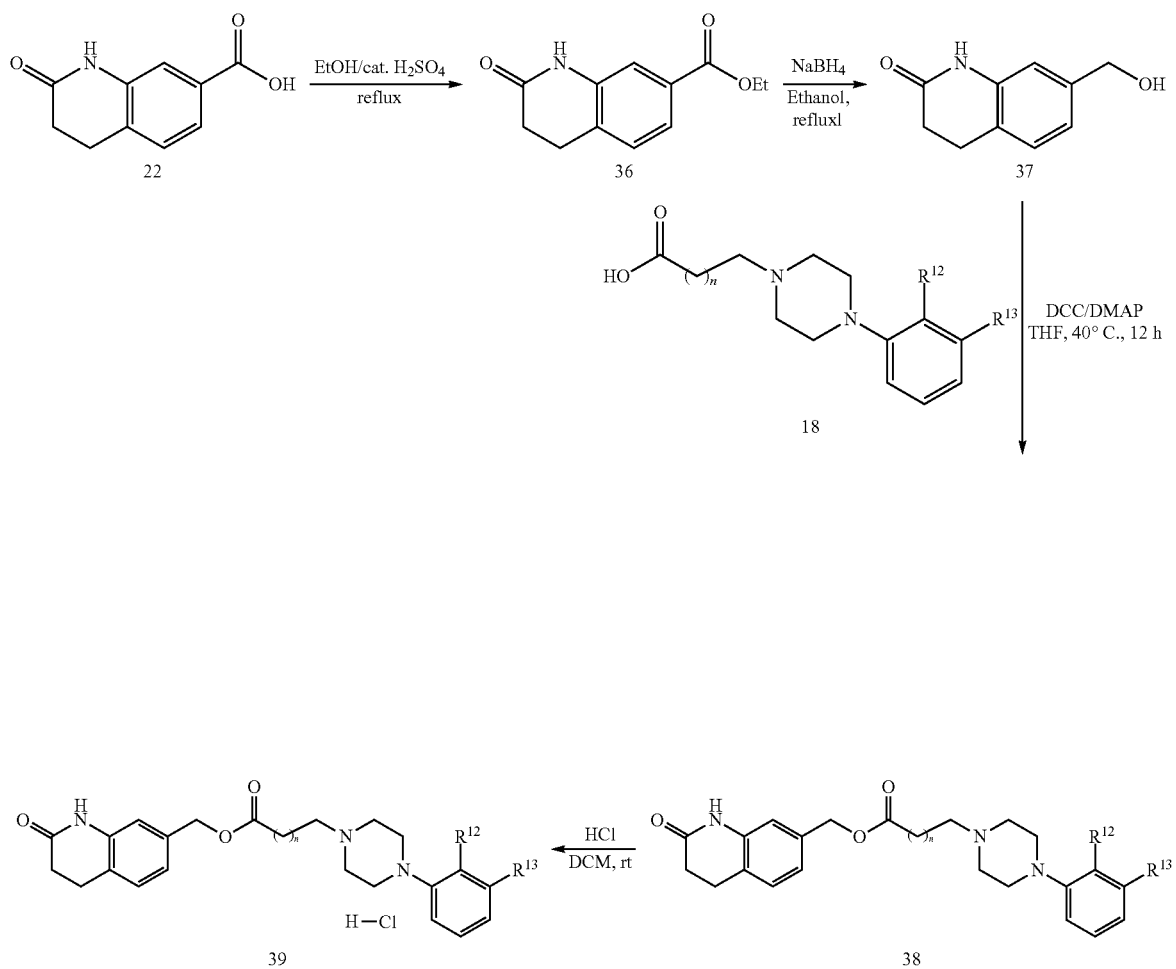

In another method selected quinolinone derivatives comprising Formulae (I)-(X) were prepared as described in Scheme 8. An appropriate piperazine carbinol (n=1, $R^{12}$=OMe, $R^{13}$=H) 21 was synthesized as illustrated in the Scheme 4. The carbinol 21 was reacted with methanesulfonyl chloride in triethylamine in DCM to give the corresponding methanesulfonyl ester 40 in good yield which was coupled with carbinol 37 in presence of a base sodium hydride in THF at around 50° C. to afford the corresponding quinolinone 41.

Scheme 8

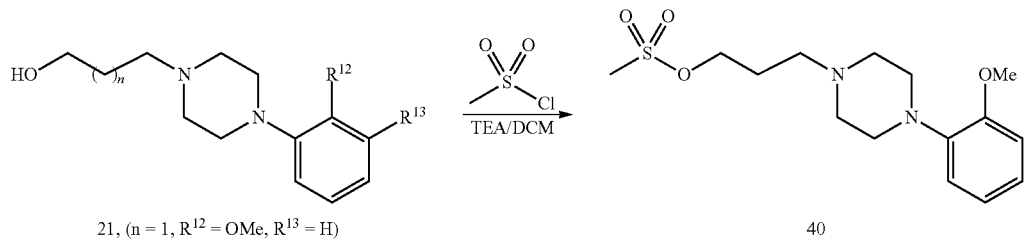

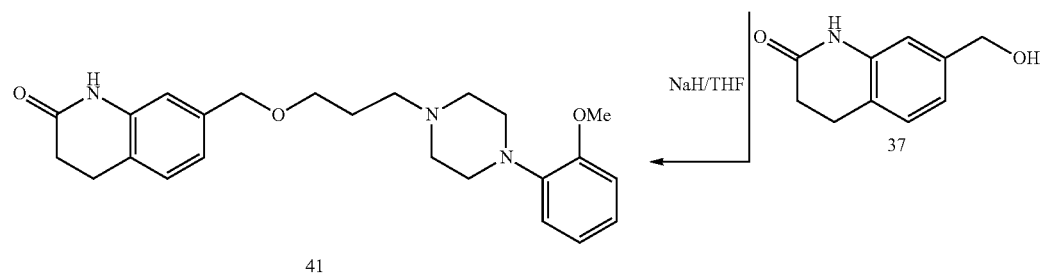

Scheme 9

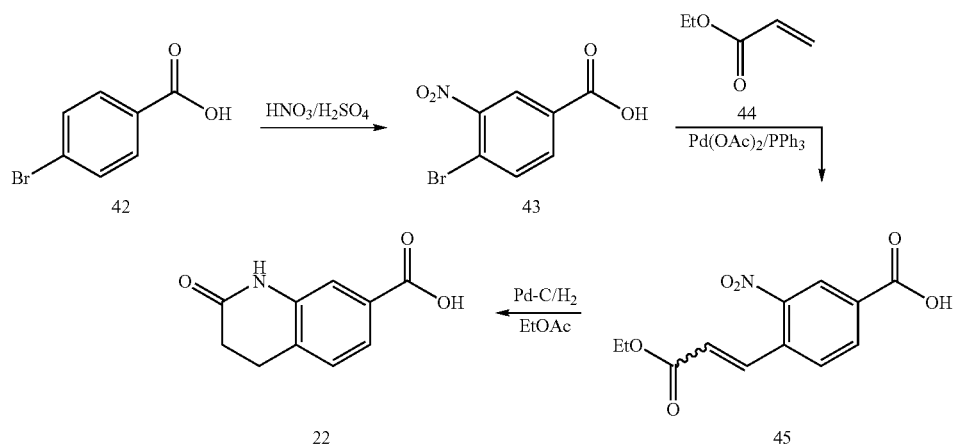

In one method the starting quinolinone carboxylic acid 22 building block used for the synthesis of compounds comprising Formulae (I)-(X) was prepared as described in Scheme 9. The commercially available 4-bromobenzoic acid 42 was nitrated under standard conditions using fuming nitric acid to give the 4-bromo-3-nitrobenzoic acid 43 in over 95% yield. The benzoic acid 43 was coupled with ethyl acrylate 44 in the presence of palladium acetate catalyst and ligand triphenylphosphine using triethylamine as base in DMF to afford the corresponding nitro substituted benzoic acid derivative 45 in over 90% yield. The reductive cyclization of the compound 45 under hydrogenation conditions using palladium over activated carbon as catalyst under hydrogen atmosphere at around 50 psi pressure gave the quinolinone carboxylic acid 22 in over 95% yield.

Therapeutic Uses of Compounds of Structural Formulae

The present invention relates to synthesis, compositions and methods of using quinolinone based compounds which are useful for treating schizophrenia and related psychoses such as acute maniac, bipolar disorder, autistic disorder and depression. The present invention provides methods for synthesizing such quinolinone based antipsychotic agents. The present invention also provides methods for using quinolinone based antipsychotic agents and composition of quinolinone based antipsychotic agents for treating schizophrenia and related psychoses such as acute maniac, bipolar disorder, autistic disorder and depression.

In accordance with the invention, a compound and/or a composition containing a compound of structural Formulae (I)-(X) is administered to a patient, preferably a human, suffering from schizophrenia. Further, in certain embodiments, the compounds and/or compositions of the invention are administered to a patient, preferably a human, as a treatment or preventive measure against acute manic, bipolar disorder, autistic disorder and depression.

Thus, those of skill in the art may readily assay and use the compounds and/or compositions containing compound(s) of structural Formulae (I)-(X) to treat a medical condition for which an antipsychotic is desired.

Therapeutic/Prophylactic Administration

The compounds, and/or compositions containing compounds(s), of structural Formulae (I)-(X) can be advantageously used in human medicine. As previously described in detail above, compounds and compositions containing compound(s) of structural Formulae (I)-(X) are useful for the treatment of schizophrenia and related psychoses such as acute manic, bipolar disorder, autistic disorder and depression.

When used to treat or prevent the above disease or disorders compounds and/or compositions of the invention can be administered or applied singly, in combination with other agents. The compounds and/or compositions of the invention can also be administered or applied singly, in combination with other pharmaceutically active agents, including other compounds and/or compositions of the invention.

The current invention provides methods of treatment and prophylaxis by administration to a patient of a therapeutically effective amount of a composition and/or compound of the invention. The patient may be an animal, is more preferably a mammal, and most preferably a human.

The present compounds and/or compositions of the invention, which comprise one or more compounds and/or compositions of the invention are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin.

In particularly, preferred embodiments, the compounds and/or compositions of the invention can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In another embodiment, polymeric materials can be used (see "Medical Applications of Controlled Release," Langer and Wise (eds.), Wiley, New York (1984); Ranger and Peppas, 1983, J. Macromol. Sci. Rev. Macromol Chem. 23:61; see also Levy et al., 1985, Science 228:190; During et al., 1989, Ann. Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described in the art (Bamba et al., Int. J. Pharm., 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems are used for oral sustained release delivery devices (See for example, Theeuwes et al., U.S. Pat. No. 3,845,770; and Theeuwes et al, U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

The compounds, and/or compositions containing compound(s) of structural Formulae (I)-(X) of the invention may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

COMPOSITIONS OF THE INVENTION

The present composition contain a therapeutically effective amount of one or more compounds of the invention, preferably in purified form, together with a suitable amount of a pharmaceutically acceptable vehicle, which so as to provide the form for proper administration to a patient. When administered to a patient, the compounds of the invention and pharmaceutically acceptable vehicles are preferably sterile. Water is preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making levigating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, $17^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about mM to about 50 mM) etc. Additionally, flavoring agents, preservatives, coloring agents, bile salts, acylcamitines and the like may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Methods of Use and Doses

A compound of the invention, or compositions thereof, will generally be used in an amount effective to achieve the intended purpose. For use to treat schizophrenia and related psychoses such as acute manic, bipolar disorder, autistic disorder and depression. The compounds of Formulae (I)-(X) and compositions containing a compound of Formulae (I)-(X) are administered or applied in a therapeutically effective amount.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day, and more preferably, once per day. Dosing may be repeated intermittently, may be provided alone or in combination with other drugs and may continue as long as required for effective treatment of the disease state or disorder.

The compounds and/or compositions containing compound(s), of structural Formulae (I)-(X) for the pharmacological treatment of schizophrenia and related psychoses such as acute maniac, bipolar disorder, autistic disorder and depression may be administered in the range 0.1 mg to 500 mg preferably 1 mg to 100 mg per day given in one or more doses and more preferably 5 mg, 10 mg, 15 mg, 20 mg, 25 mg, 35 mg or 50 mg per day and most preferably 25 mg.

The compounds of the invention are preferably assayed in vitro and in vivo, for the desired therapeutic or prophylactic activity, prior to use in humans. The compounds of the invention may also be demonstrated to be effective and safe using animal model systems.

Preferably, the therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, composition comprising a compound of the invention is administered concurrently with the administration of another therapeutic agent, which can be part of the same composition. In another embodiment, a composition comprising a compound of the invention is administered prior or subsequent to administration of another therapeutic agent.

EXAMPLES

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

| | |
|---|---|
| Atm = | Atmosphere |
| DCM = | dichloromethane |
| DMAP = | 4-N,N-dimethylaminopyridine |
| DMF = | N,N-dimethylformamide |
| g = | gram |
| h = | hours |
| L = | liter |
| LC/MS = | liquid chromatography/mass spectroscopy |
| M = | molar |
| mL = | milliliter |
| mmol = | millimols |
| nM = | nanomolar |
| μM = | micromolar |
| MTBE = | methyl tert-butyl ether |
| rt = | room temperature |
| TEA = | triethylamine |
| THF = | tetrahydrofuran |
| TFA = | trifluoroacetic acid |

Example 1

7-(4-Bromobutoxy)-3,4-dihydroquinolinone-2(1H)-one (3) (Scheme 1)

To a stirred suspension of anhydrous potassium carbonate ($K_2CO_3$) (10.50 g, 0.075 mol) in 100 mL of anhydrous N,N-dimethylformamide (DMF) was added 7-hydroxyquinolinone 1 (10.00 g, 0.06 mol) followed by 1,4-dibromobutane 2 (25.91 g, 0.12 mol). The resulting mixture was heated at 60° C. for 12 h. The progress of the reaction was monitored by thin layer chromatography (TLC) technique. After cooling to room temperature, the reaction mixture was filtered through a sintered funnel and the precipitate was washed with ethyl acetate (25 mL×2). The combined filtrate was concentrated on a rotavapor. The residue was diluted with 250 mL of ethyl acetate, washed with water (100 mL×2), dried over anhydrous magnesium sulfate and evaporated the solvent. The residue was triturated with hexane and then filtered the precipitate to give the pure title compound 3. White solid, 12.88 g (72%). $^1$H NMR (400 MHz, $CDCl_3$): δ 1.92-1.97 (m, 2H); 2.05-2.10 (m, 2H); 2.64 (t, J=9.2 Hz, 2H); 2.92 (t, J=9.2 Hz, 2H); 3.50 (t, J=7.6 Hz, 2H); 3.98 (t, J=7.6 Hz, 2H); 6.37 (d, J=3.2 Hz, 1H); 6.50-6.54 (m, 1H); 7.04 (d, J=11.2 Hz, 1H), 8.61 (broad s, 1H).

Example 2

7-(4-(4-(2-Methoxyphenyl)piperazin-1-yl)butoxy)-3,4-dihydroquinolin-2(1H)-one (5) (Scheme 1)

To a mixture of 7-(4-bromobutoxy)-3,4-dihydroquinolin-2(1H)-one (3) (13 g, 0.0437 mol) and the commercially available (purchased from Sigma-Aldrich) 1-(2-methoxy-phenyl)piperazine hydrochloride (4) (0.0437 mol) in 60 mL anhydrous acetonitrile at ice-bath temperature was added N,N-diisopropylethylamine (DIEA) (19 mL, 0.11 mol). The resulting mixture was refluxed for overnight (12 h). The progress of the reaction was monitored by thin layer chromatography (TLC). The reaction mixture was concentrated on rotavapor, the residue was dissolved in dichloromethane (150 mL), washed with water (100 mL×2), dried over sodium sulphate ($Na_2SO_4$) and evaporated under reduced pressure. The residue was triturated with methyl tert-butyl ether (MTBE) and filtered to give the corresponding quinolinone 5. White solid, 12.4 g (70%). $^1$H NMR (400 MHz, $CDCl_3$): δ 1.64-1.86 (4H, m); 2.55 (t, J=9.2 Hz, 2H); 2.63 (t, J=9.2 Hz, 2H); 2.75 (broad s, 4H); 2.91 (t, J=9.2 Hz, 2H); 3.16 (broad s, 4H); 3.88 (s, 3H); 3.98 (t, J=7.6 Hz, 2H); 6.32 (d, J=2.8 Hz, 1H); 6.53 (dd, J=3.2, 11.2 Hz, 1H); 6.87 (d, J=10 Hz, 1H); 6.94-7.06 (m, 4H), 7.83 (broad s, 1H). MS (ESI): m/z=410.3 (M+H$^+$).

Example 3

7-(4-(4-(2-Hydroxyphenyl)piperazin-1-yl)butoxy)-3,4-dihydroquinolin-2(1H)-one (6) (Scheme 1)

To a solution of 7-(4-(4-(2-methoxyphenyl)piperazin-1-yl)butoxy)-3,4-dihydroquinolin-2(1H)-one (5) (6.3 g, 0.015 mol) in 24 mL dichloromethane and 24 mL ethanethiol cooled to ice-bath temperature was added aluminum chloride (6.15 g, 0.046 mol) in small portions. The resulting mixture was stirred at room temperature for 12 h. The progress of the reaction was monitored by thin layer chromatography (TLC). The reaction mixture was decanted and the sticky mass was dissolved in water by stirring for 1 h. The pH of the resulting aqueous solution was adjusted to pH=7 by adding 2M sodium hydroxide (NaOH) solution. Copious amount of acetone was added and the resulting thick paste was filtered and washed with acetone followed by dichloromethane, the combined filtrate was evaporated. The residue was purified by silica gel column chromatography using 0-100% gradient of hexanes and ethyl acetate to give the pure quinolinone 6. White solid, 1.3 g (20%). $^1$H NMR (400 MHz, CDCl$_3$): δ 1.52-1.59 (m, 2H); 1.66-1.73 (m, 2H); 2.32-2.40 (m, 4H), 2.47 (broad s, 4H), 2.75 (t, J=8 Hz, 2H); 2.90 (broad s, 4H), 3.89 (t, J=6.4 Hz, 2H); 6.41 (d, J=2.4 Hz, 1H); 6.46 (dd, J=2.4, 8 Hz, 1H); 6.67-6.84 (m, 4H); 7.01 (d, J=8.4 Hz, 1H); 8.88 (s, 1H); 9.96 (s, 1H). MS (ESI): m/z=396.5 (M+H$^+$).

Example 4

Ethyl 4-(2-(4-(4-(2-oxo-1,2,3,4-tetrahydroquinolin-7-yloxy)butyl)piperazin-1-yl)phenoxy)butanoate (8a) (Scheme 1)

A mixture of 7-(4-(4-(2-hydroxyphenyl)piperazin-1-yl)butoxy)-3,4-dihydroquinolin-2(1H)-one (6) (0.2 g, 0.0005 mol), the halide 7b (0.0005 mol) and cesium carbonate (0.16 g, 0.0005 mol) in 10 mL anhydrous DMF was heated at 60° C. for 12 h. The reaction mixture was diluted with 50 mL ethyl acetate, filtered, washed the precipitate with ethyl acetate, the combined filtrates was washed with water (250 mL×2), dried (MgSO$_4$) and evaporated to give the corresponding O-alkylated compound 8a which was purified by silica gel chromatography using a gradient of hexane and ethyl acetate to give the pure compound 8a. Colorless oil (0.25 g, 98%). $^1$H NMR (400 MHz, CDCl$_3$): δ 1.22-1.26 (m, 3H); 1.79 (broad s, 4H); 2.14 (quintet, J=7.2 Hz, 2H); 2.53-2.75 (m, 6H); 2.85 (broad s, 4H); 2.87 (t, J=8.0 Hz, 2H); 3.16 (broad s, 4H); 3.95 (t, J=5.2 Hz, 2H); 4.02 (t, J=6.4 Hz, 2H); 4.07-4.16 (m, 2H); 6.34-6.40 (m, 1H); 6.46-6.52 (m, 1H); 6.82-6.84 (m, 1H); 6.90-6.97 (m, 3H); 7.01-7.03 (m, 1H); 8.70 (broad s, 1H). MS (ESI): m/z=510.2 (M+H$^+$).

Example 5

Isopropyl 4-(2-(4-(4-(2-oxo-1,2,3,4-tetrahydroquinolin-7-yloxy)butyl)piperazin-1-yl)phenoxy)butanoate (8b) (Scheme 1) was prepared from the compound 6 and the halide 7c by following the same protocol described for the synthesis of 8a (Example 4). Colorless oil (0.2 g, 76%). $^1$H NMR (400 MHz, CDCl$_3$): δ1.19 (d, J=6.4 Hz, 6H); 1.66-1.71 (m, 2H); 1.75-1.80 (m, 2H); 2.12 (t, J=7.2 Hz, 2H); (m, 6H); 2.56-2.67 (m, 6H); 3.08 (broad s, 4H); 3.93 (t, J=6.4 Hz, 2H); 4.00 (t, J=6.4 Hz, 2H); 4.98 (quintet, J=6.4 Hz, 1H); 6.35 (d, J=2.8 Hz, 1H); 6.49 (dd, J=2.4, 8.4 Hz, 1H); 6.81 (d, J=8.4 Hz, 1H); 6.87-6.95 (m, 3H); 6.70 (d, J=8.4 Hz, 1H); 8.59 (broad s, 1H). MS (ESI): m/z=524.30 (M+H$^+$).

Example 6

Ethyl 3-(2-(2-(4-(4-(2-oxo-1,2,3,4-tetrahydroquinolin-7-yloxy)butyl)piperazin-1-yl)phenoxy)-acetamido)propanoate (8c) (Scheme 1) was prepared from the compound 6 and the halide 7d by following the same protocol described for the synthesis of 8a (Example 4). Colorless oil (0.1 g, 36%). $^1$H NMR (400 MHz, CDCl$_3$): δ 1.15 (t, J=7.2 Hz, 3H); 1.35-1.43 (m, 2H); 1.64-1.74 (m, 2H); 1.78-1.83 (m, 2H); 2.52 (t, J=6.4 Hz, 2H); 2.58 (t, J=8.0 Hz, 2H); 2.69 (broad s, 4H); 2.86 (t, J=6.8 Hz, 2H); 3.09 (broad s, 4H); 3.55 (q, J=6.8 Hz, 2H); 3.94 (t, J=6.4 Hz, 2H); 4.19 (t, J=6.4 Hz, 2H); 4.57 (s, 2H); 6.38 (d, J=2.4 Hz, 1H); 6.49 (dd, J=2.4, 8.4 Hz, 1H); 6.89-6.92 (m, 1H); 6.98-7.03 (m, 3H); 7.49-7.69 (m, 1H); 8.34 (t, J=6.0 Hz, 1H); 9.00 (broad s, 1H). MS (ESI): m/z=553.30 (M+H$^+$).

Example 7

Ethyl 2-(4-(2-(4-(4-(2-oxo-1,2,3,4-tetrahydroquinolin-7-yloxy)butyl)piperazin-1-yl)phenoxy)-butanamido)acetate (8d) (Scheme 1) was prepared from the compound 6 and the halide 7e by following the same protocol described for the synthesis of 8a (Example 4). Colorless oil (0.1 g, 35%). $^1$H NMR (400 MHz, CDCl$_3$): δ 1.21 (t, J=7.2 Hz, 3H); 1.35-1.45 (m, 2H); 1.61-1.71 (m, 2H); 1.75-1.80 (m, 2H); 2.14 (quintet, J=6.6 Hz, 2H); 2.42-2.50 (m, 4H); 2.55 (t, J=8.0 Hz, 2H); 2.65 (broad s, 4H); 2.83 (t, J=7.6 Hz, 2H); 3.08 (broad s, 4H); 3.90-3.92 (m, 2H); 4.04 (q, J=7.2 Hz, 2H); 4.18 (t, J=7.0 Hz, 2H); 6.36 (d, J=2.0 Hz, 1H); 6.47 (dd, J=2.4, 8.4 Hz, 1H); 6.82-6.99 (m, 5H); 8.95 (broad s, 2H). MS (ESI): m/z=567.30 (M+H$^+$).

Example 8

Ethyl 4-(2-(4-(4-(2-oxo-1,2,3,4-tetrahydroquinolin-7-yloxy)butyl)piperazin-1-yl)phenoxy)butanoat hydrochloride (9a) (Scheme 1)

To a solution of the free base 8a (0.1-0.3 g) in 2 mL dichloromethane was added 4 mL 2M HCl solution in diethyl ether. The mixture was stirred at room temperature for 30 minutes. The solvent was evaporated, residue was triturated with ether, and solid precipitated was filtered, washed with ether and dried to give the corresponding hydrochloride (HCl) salt 9a. The compound 9a gave satisfactory 1H NMR data. Off-white solid, 0.24 g (83%). MS (ESI): m/z=510.20 (M+H$^+$).

Example 9

Isopropyl 4-(2-(4-(4-(2-oxo-1,2,3,4-tetrahydroquinolin-7-yloxy)butyl)piperazin-1-yl)phenoxy)butanoate hydrochloride (9b) (Scheme 1) was prepared from 8b by following the same protocol described for the compound 9a. (Example 8). The compound 9b gave satisfactory 1H NMR data. Off-white solid, 0.015 g (17%). MS (ESI): m/z=524.30 (M+H$^+$).

Example 10

Ethyl 3-(2-(2-(4-(4-(2-oxo-1,2,3,4-tetrahydroquinolin-7-yloxy)butyl)piperazin-1-yl)phenoxy)-acetamido)propanoate (9c) (Scheme 1) was prepared from 8c by following the same protocol described for the compound 9a. (Example 8). The compound 9c gave satisfactory 1H NMR data. Off-white solid, 0.063 g (59%). MS (ESI): m/z=553.3 (M+H$^+$).

Example 11

Ethyl 2-(4-(2-(4-(4-(2-oxo-1,2,3,4-tetrahydroquinolin-7-yloxy)butyl)piperazin-1-yl)phenoxy)-butanamido)acetate hydrochloride (9d) (Scheme 1) was prepared from 8d by following the same protocol described for the compound 9a.

(Example 8). The compound 9d gave satisfactory 1H NMR data. Brown solid, 0.036 g (34%). MS (ESI): m/z=567.3 (M+H$^+$).

Example 12 tert-Butyl 4-(2-hydroxyphenyl)piperazine-1-carboxylate (12) (Scheme 2)

To a stirred suspension of 1-(2-hydroxyphenyl)piperazine (10) (1.78 g, 0.01 mol) in 20 mL tetrahydrofuran (in a round bottom flask fitted with a gas bubbler) was added a solution of di-tert-butylcarbonate 11 (2.62 g, 0.012 mol) in 10 mL tetrahydrofuran at room temperature. Soon it became a clear solution and a gas was evolved. The resulting mixture was heated at 60° C. for 6 h. The progress of the reaction was monitored by thin layer chromatography (TLC). The solvent was evaporated, the residue was dissolved in ethyl acetate (100 mL) and washed with water (100 mL×2), dried over sodium sulphate (Na$_2$SO$_4$) and evaporated. The residue was triturated with MTBE and filtered to give the compound 12. White solid, 2.5 g (92%). $^1$H NMR (400 MHz, CDCl$_3$): δ 1.49 (s, 9H); 2.81 (t, J=4.8 Hz, 4H); 3.58 (t, J=4.8 Hz, 4H); 6.84-6.88 (m, 1H); 6.94-6.99 (m, 1H); 7.06-7.12 (m, 2H). MS (ESI): m/z=279.50 (M+H$^+$).

Example 13 tert-Butyl 4-(2-(2-oxoethoxy)phenylpiperazine-1-carboxylate (13a) (Scheme 2)

A mixture of tert-butyl 4-(2-hydroxyphenyl)piperazine-1-carboxylate (12) (0.5 g, 0.0018 mol), halide 7a (0.0035 mol) and cesium carbonate (0.59 g, 0.0018 mol) in 10 mL of anhydrous DMF was heated at 60° C. for 12 h. The progress of the reaction was monitored by thin layer chromatography (TLC). The reaction mixture was diluted with 50 mL of ethyl acetate, filtered, washed the precipitate with ethyl acetate, the combined filtrate was washed with water (50 mL×2), dried (MgSO$_4$) and evaporated. The residue was purified by silica gel chromatography using a gradient of hexane and ethyl acetate to give the pure compound 13a. Colorless oil, 0.4 g (61%). $^1$H NMR (400 MHz, CDCl$_3$): δ 1.25 (t, J=7.2 Hz, 3H); 1.43 (s, 9H); 3.01 (t, J=4.8 Hz, 4H); 3.56 (t, J=4.8 Hz, 4H); 4.19 (q, J=7.2 Hz, 2H); 4.62 (s, 2H); 6.72-6.75 (m, 1H); 6.86-6.93 (m, 3H). MS (ESI): m/z=365.50 (M+H$^+$).

Example 14

(S)-tert-Butyl 4-(2-(2-(1-ethoxy-3-methyl-1-oxobutan-2-ylamino)-2-oxoethoxy)phenyl)-piperazine-1-carboxylate (13b) (Scheme 2) was synthesized from the compound 12 and the halide 7f by following the same protocol described for the synthesis of the compound 13a (Example 13). Colorless oil, 0.37 g (45%). $^1$H NMR (400 MHz, CDCl$_3$): δ 0.83 (d, J=7.0 Hz, 6H); 0.90 (d, J=7.0 Hz, 3H); 1.24 (t, J=7.0 Hz, 3H); 1.47 (s, 9H); 2.08-2.17 (m, 1H); 2.90-3.12 (m, 4H); 3.60-3.70 (m, 4H); 4.15-4.22 (m, 2H); 6.91-6.93 (m, 1H); 6.98-7.04 (m, 2H); 7.50-7.56 (m, 1H). MS (ESI): m/z=464.50 (M+H$^+$).

Example 15

Ethyl 2-(2-(4-(4-(2-oxo-1,2,3,4-tetrahydroquinolin-7-yloxy)butyl)piperazin-1-yl)phenoxy)acetate (14a) (Scheme 2)

A solution of the N—BOC protected piperazine 13a (0.0015 mol) in 1:1 trifluoroacetic acid and dichloromethane (15 mL) was stirred at room temperature for 8 h (monitored by TLC). After evaporation of TFA and DCM, the residue was dissolved in 5 mL of anhydrous acetonitrile, and then, added N,N-diisopropylethylamine (DIEA) (0.5 mL, 0.003 mol) followed by the compound 3 (0.45 g, 0.0015 mol). The resulting mixture was heated at 70° C. for 6 h. The progress of the reaction was monitored by thin layer chromatography (TLC). The solvent was evaporated; residue was diluted with 50 mL dichloromethane, washed with water (25 mL×2) and dried over anhydrous magnesium sulfate (MgSO$_4$). After evaporation of the solvent, the corresponding N-alkylated product 14a was purified by silica gel column chromatography using a gradient of hexane and ethyl acetate to give the pure compound 14a. Colorless oil, 0.2 g (28%). $^1$H NMR (400 MHz, CDCl$_3$): δ 1.23 (t, J=7.2 Hz, 3H); 1.41-1.72 (m, 2H); 1.75-1.80 (m, 2H); 2.45 (t, J=7.6 Hz, 2H); 2.58 (t, J=8.0 Hz, 2H); 2.65 (broad s, 4H); 2.86 (t, J=7.2 Hz, 2H); 3.14 (broad s, 4H); 3.93 (t, J=6.4 Hz, 2H); 4.24 (q, J=7.2 Hz, 2H); 4.65 (s, 2H); 6.36 (d, J=2.4 Hz, 1H); 6.49 (dd, J=2.8, 8.4 Hz, 1H); 6.75-6.78 (m, 1H); 6.89-6.95 (m, 2H); 7.00 (d, J=8.4 Hz, 1H); 7.49-7.69 (m, 1H); 8.91 (broad s, 1H). MS (ESI): m/z=482.20 (M+H$^+$).

Example 16

(S)-Ethyl 3-methyl-2-(2-(2-(4-(4-(2-oxo-1,2,3,4-tetrahydroquinolin-7-yloxy)butyl)piperazin-1-yl)phenoxy)acetamido)butanoate (14b) (Scheme 2) was synthesized from the compounds 3 and 13b by following the protocol described for the compound 14a (Example 15). Colorless oil, 0.27 g (58%). $^1$H NMR (400 MHz, CDCl$_3$): δ 0.83 (d, J=7.0 Hz, 3H); 0.90 (d, J=7.0 Hz, 3H); 1.24 (t, J=7.2 Hz, 3H); 1.60-1.69 (m, 2H); 1.74-1.79 (m, 2H); 2.13 (quintet, J=6.4 Hz, 1H); 2.43 (t, J=7.2 Hz, 2H); 2.55 (t, J=7.2 Hz, 2H); 2.65 (broad s, 4H); 2.82 (t, J=7.2 Hz, 2H); 3.01-3.13 (m, 4H); 3.90 (t, J=6.0 Hz, 2H); 4.05 (q, J=7.2 Hz, 2H); 4.53-4.56 (m, 1H); 4.60 (two s, 2H); 6.39 (d, J=2.4 Hz, 1H); 6.45-6.47 (m, 1H); 6.84-6.87 (m, 1H); 6.92-6.95 (m, 3H); 7.56 (d, J=9.2 Hz, 1H); 9.46 (broad s, 2H). MS (ESI): m/z=581.30 (M+H$^+$).

Example 17

Ethyl 2-(2-(4-(4-(2-oxo-1,2,3,4-tetrahydroquinolin-7-yloxy)butyl)piperazin-1-yl)phenoxy)acetate hydrochloride (15a) (Scheme 2)

To a solution of the compound 14a (0.2-0.3 g) in 2 mL dichloromethane was added 4 mL 2M HCl solution in diethyl ether. The mixture was stirred at room temperature for 30 minutes. The solvent was evaporated, residue was triturated with MTBE, and solid precipitated was filtered, washed with ether and dried to give the corresponding hydrochloride 15a. The hydrochloride salt 15a gave satisfactory 1H NMR spectral data. Off-white solid, 0.14 g (65%). MS (ESI): m/z=482.2 (M+H$^+$).

Example 18

(S)-Ethyl 3-methyl-2-(2-(2-(4-(4-(2-oxo-1,2,3,4-tetrahydroquinolin-7-yloxy)butyl)piperazin-1-yl)phenoxy)-acetamido)butanoate (15b) (Scheme 2) was prepared from the compound 14b according to the protocol described for the compound 15a (Example 17). The hydrochloride salt 15b gave satisfactory 1H NMR spectral data. Off-white solid, 0.24 g (88%). MS (ESI): m/z=581.3 (M+H$^+$).

Example 19

Ethyl 3-(4-(2-methoxyphenyl)piperazin-1-yl)propanoate (17a) (Scheme 3)

To a mixture of ethyl 3-bromopropionate (16) (5.6 mL, 0.0437 mol) and 1-(2-methoxyphenyl)piperazine hydrochloride (4a) (0.0437 mol) in 60 mL of anhydrous acetonitrile at ice-bath temperature was added N,N-diisopropylethylamine (DIEA) (19 mL, 0.11 mol). The resulting mixture was stirred at 60° C. for overnight. The progress of the reaction was monitored by thin layer chromatography (TLC). The reaction mixture was concentrated on rotavapor, the residue was dissolved in dichloromethane and washed with water, dried over sodium sulphate ($Na_2SO_4$) and evaporated under reduced pressure to give the corresponding title compound 17a which was purified by silica gel chromatography using a gradient of hexane and ethyl acetate. Colorless oil, 12.1 g (95%). $^1$H NMR (400 MHz, $CDCl_3$): δ 1.23 (t, J=7.2 Hz, 3H); 2.51 (t, J=7.6 Hz, 2H); 2.65 (broad s, 4H); 2.74 (t, J=7.6 Hz, 2H); 3.06 (broad s, 4H); 3.83 (s, 3H); 4.11 (q, J=7.2 Hz, 2H); 6.81-6.98 (m, 4H). MS (ESI): m/z=293.40 (M+H$^+$).

Example 20

Ethyl 3-(4-(2,3-dichlorophenyl)piperazin-1-yl)propanoate (17b) (Scheme 3) was synthesized from ethyl 3-bromopropionate 16 and the piperazine 4 ($R^{12}=R^{13}=Cl$) according to the protocol described for 17a (Example 19). Off-white solid, 1.6 g (11%). $^1$H NMR (400 MHz, $CDCl_3$): δ 1.22 (t, J=7.2 Hz, 3H); 2.51 (t, J=7.6 Hz, 2H); 2.62 (broad s, 4H); 2.73 (t, J=7.6 Hz, 2H); 3.01 (broad s, 4H); 4.12 (q, J=7.2 Hz, 2H); 6.89-6.92 (m, 1H); 7.08-7.11 (m, 2H). MS (ESI): m/z=331.40 (M+H$^+$).

Example 21

Ethyl 4-(4-(2-methoxyphenyl)piperazin-1-yl)butanoate (17c) (Scheme 3) was synthesized from ethyl 4-bromobutanoate 16 and the piperazine 4 ($R^{12}=OMe, R^{13}=H$) according to protocol described for 17a (Example 19). Brown oil, 9.6 g (99%). $^1$H NMR (400 MHz, $CDCl_3$): δ 1.23 (t, J=7.2 Hz, 3H), 1.82 (quintet, J=7.2 Hz, 2H); 2.35 (t, J=7.2 Hz, 2H); 2.43 (t, J=7.2 Hz, 2H); 2.63 (broad s, 4H); 3.07 (broad s, 4H); 3.84 (s, 3H); 4.13 (q, J=7.2 Hz, 2H); 6.83-6.99 (m, 4H). MS (ESI): m/z=307.50 (M+H$^+$).

Example 22

Ethyl 4-(4-(2,3-dichlorophenyl)piperazin-1-yl)butanoate (17d) (Scheme 3) was synthesized from ethyl 4-bromobutanoate 16 and the piperazine 4 ($R^{12}=R^{13}=Cl$) according to protocol described for 17a (Example 19). Yellow oil, 3.2 g (93%). $^1$H NMR (400 MHz, $CDCl_3$): δ 1.24 (t, J=7.2 Hz, 3H), 1.83 (quintet, J=7.2 Hz, 2H); 2.34 (t, J=7.2 Hz, 2H); 2.42 (t, J=7.2 Hz, 2H); 2.61 (broad s, 4H); 3.03 (broad s, 4H); 4.12 (q, J=7.2 Hz, 2H); 6.90-6.96 (m, 1H); 7.09-7.14 (m, 2H). MS (ESI): m/z=345.40 (M+H$^+$).

Example 23

3-(4-(2-Methoxyphenyl)piperazin-1-yl)propanoic acid (18a) (Scheme 3)

To a solution of ethyl 3-(4-(methoxyphenyl)piperazin-1-yl)propanoate 17a (1.17 g, 0.004 mol) in 8 mL ethanol was added 4 mL 2N aq. sodium hydroxide solution. The resulting mixture was stirred at room temperature for overnight. The progress of the reaction was monitored by thin layer chromatography (TLC). The reaction mixture was concentrated on rotavapor under reduced pressure and the residue was cooled in ice bath. A few pieces of crushed ice were introduced into the flask and then acidified with 1N HCl solution. The reaction mixture was saturated with NaCl and extracted with dichloromethane, dried over sodium sulfate ($Na_2SO_4$) and evaporated to give the title carboxylic acid 18a which was carried to next step without any further purification. Colorless oil, 0.5 g (47%). $^1$H NMR (400 MHz, $CDCl_3$): δ 2.57 (t, J=6.0 Hz, 2H); 2.94 (t, J=6.0 Hz, 2H); 3.01 (broad s, 4H); 3.21 (broad s, 4H); 3.83 (s, 3H); 6.87 (d, J=7.6 Hz, 1H); 6.92 (d, J=4.0 Hz, 2H); 7.01-7.05 (m, 1H). MS (ESI): m/z=265.40 (M+H$^-$).

Example 24

3-(4-(2,3-Dichlorophenyl)piperazin-1-yl)propanoic acid (18b) (Scheme 3) was synthesized from the ester 17b according to the protocol described for the compound 18a (Example 23). White solid, 1.12 g (93%). $^1$H NMR (400 MHz, $CDCl_3$): δ 2.59 (t, J=6.0 Hz, 2H); 2.91 (t, J=6.0 Hz, 2H); 2.95 (broad s, 4H); 3.18 (broad s, 4H); 6.96 (dd, J=2.0, 8.0 Hz, 1H); 7.15-7.23 (m, 2H). MS (ESI): m/z=303.30 (M+H$^-$).

Example 25

4-(4-(2-Methoxyphenyl)piperazin-1-yl)butanoic acid (18c) (Scheme 3) was prepared from the ester 17c according to the standard protocol described for 18a (Example 23). White solid, 0.9 g (49%). $^1$H NMR (400 MHz, $CDCl_3$): δ 1.87 (quintet, J=5.6 Hz, 2H); 2.60 (t, J=5.6 Hz, 2H); 2.76 (t, J=5.6 Hz, 2H); 2.96 (broad s, 4H); 3.20 (broad s, 4H); 3.85 (s, 3H); 6.85-6.92 (m, 3H), 7.00-7.05 (m, 1H).

Example 26

4-(4-(2,3-Dichlorophenyl)piperazin-1-yl)butanoic acid 18d (Scheme 3) was prepared from the ester 17d according to the standard protocol described for 18a (Example 23). White solid, 1.4 g (99%). $^1$H NMR (400 MHz, $CDCl_3$): δ 1.88 (quintet, J=5.6 Hz, 2H); 2.63 (t, J=5.6 Hz, 2H); 2.78 (t, J=5.6 Hz, 2H); 2.95 (broad s, 4H); 3.18 (broad s, 4H); 6.96 (dd, J=1.6 Hz, 7.6 Hz, 1H); 7.14-7.21 (m, 2H). MS (ESI): m/z=317.30 (M+H$^+$).

Example 27

2-Oxo-1,2,3,4-tetrahydroquinolin-7-yl 4-(4-(2-methoxyphenyl)piperazin-1-yl)butanoate (19a) (Scheme 3)

To a mixture of 4-(4-(methoxy-phenyl)piperazin-1-yl)butanoic acid (18a) (0.0012 mol) and 7-hydroxy-3,4-dihydroquinolin-2(1H)-one (1) (0.2 g, 0.0012 mol) in 25 mL dichloromethane was added dicyclohexylcarbodiimide (0.25 g, 0.0012 mol) followed by 4-(dimethylamino)pyridine (0.15 g, 0.0012 mol). The resulting mixture was refluxed for 3 hours. The progress of the reaction was monitored by thin layer chromatography (TLC). The reaction mixture was filtered and the precipitate was washed with dichloromethane. The combined filtrate was washed with 100 mL water (50 mL×2), dried ($Na_2SO_4$) and evaporated under reduced pressure to give title compound 19a which was purified by silica gel column chromatography using ethyl acetate as eluent. Colorless oil, 0.1 g (19%). $^1$H NMR (400 MHz, $CDCl_3$): δ 1.94

(quintet, J=8.0 Hz, 2H); 2.48 (t, J=6.8 Hz, 2H); 2.56-2.60 (m, 4H); 2.66 (broad s, 4H); 2.89 (t, J=7.6 Hz, 2H); 3.07 (broad s, 4H); 3.82 (s, 3H); 6.59-6.61 (m, 1H); 6.66-6.70 (m, 1H); 6.38-6.98 (m, 4H); 7.03-7.10 (m, 1H). MS (ESI): m/z=424.10 (M+H$^+$).

Example 28

2-Oxo-1,2,3,4-tetrahydroquinolin-7-yl 4-(4-(2,3-dichlorophenyl)piperazin-1-yl)butanoate (19b) (Scheme 3) was synthesized from the compound 18b according to the procedure described for 19a (Example 27). White solid, 0.37 g (25%). $^1$H NMR (400 MHz, CDCl$_3$): δ 1.81 (quintet, J=8.0 Hz, 2H); 2.39-2.62 (m, 10H); 2.85 (t, J=9.2 Hz, 2H); 2.97 (broad s, 4H); 6.59 (d, J=2.8 Hz, 1H); 6.65 (dd, J=2.8, 11.2 Hz, 1H); 7.08-7.17 (m, 2H); 7.27-7.29 (m, 2H). MS (ESI): m/z=462.2 (M$^+$). MS (ESI): m/z=462.10 (M+H$^+$).

Example 29

2-Oxo-1,2,3,4-tetrahydroquinolin-7-yl 4-(4-(2-methoxyphenyl)piperazin-1-yl)butanoate hydrochloride (20a) (Scheme 3)

To a solution of the 2-oxo-1,2,3,4-tetrahydroquinolin-7-yl 4-(4-(methoxy-phenyl)piperazin-1-yl)butanoate (19a) (0.1 g) in 2 mL dichloromethane was added 4 mL 2M HCl solution in diethyl ether. The mixture was stirred at room temperature for 30 minutes. The solvent was evaporated, residue was triturated with ether, and solid precipitated was filtered, washed with ether and dried to give 2-oxo-1,2,3,4-tetrahydroquinolin-7-yl 4-(4-(2-methoxyphenyl)piperazin-1-yl)butanoate hydrochloride 20a. The hydrochloride salt 20a gave satisfactory 1H NMR spectral data. White solid, 0.106 g (98%). MS (ESI): m/z=424.1 (M+H$^+$).

Example 30

2-Oxo-1,2,3,4-tetrahydroquinolin-7-yl 4-(4-(2,3-dichlorophenyl)piperazin-1-yl)butanoate hydrochloride (20b) (Scheme 3) was prepared from the compound 19b according to the protocol described for the compound 20a (Example 29). The hydrochloride salt 20b gave satisfactory 1H NMR spectral data. White solid, 0.11 g (98%). MS (ESI): m/z=462.1 (M$^+$).

Example 31

3-(4-(2-Methoxyphenyl)piperazin-1-yl)propan-1-ol 21a (Scheme 4)

A mixture of ethyl 3-(4-(methoxyphenyl)piperazin-1-yl) propanoate (17a) (0.0048 mol) and sodium borohydride (5.4 g, 0.14 mol) in 100 mL anhydrous ethanol was refluxed for overnight (12 h). The progress of the reaction was monitored by thin layer chromatography (TLC). The reaction mixture was concentrated on rotavapor. The residue was diluted with DCM, washed with saturated aqueous NaHCO$_3$ solution (25 mL×2) and water (25 mL), dried over sodium sulphate (Na$_2$SO$_4$) and evaporated under reduced pressure to give 3-(4-(methoxyphenyl)piperazin-1-yl)propan-1-ol (21a) which was purified by silica gel column chromatography using 0-5% gradient of ethyl acetate and methanol. White solid, 0.6 g (50%). $^1$H NMR (400 MHz, CDCl$_3$): δ 1.75 (quintet, J=5.2 Hz, 2H); 2.69 (t, J=6.0 Hz, 2H); 2.74 (broad s, 4H); 3.08 (broad s, 4H); 3.82 (t, J=5.2 Hz, 2H); 3.85 (s, 3H); 5.35 (broad s, 1H); 6.84-6.86 (m, 1H); 6.90-6.93 (m, 2H); 6.97-7.02 (m, 1H). MS (ESI): m/z=251.40 (M+H$^+$).

Example 32

3-(4-(2,3-Dichlorophenyl)piperazin-1-yl)propan-1-ol (21b) (Scheme 4) was synthesized from 17b according to the protocol described for 21a (Example 31). White solid, 0.96 g (69%). $^1$H NMR (400 MHz, CDCl$_3$): δ 1.76 (quintet, J=5.2 Hz, 2H); 2.70 (t, J=6.0 Hz, 2H), 2.73 (broad s, 4H); 3.05 (broad s, 4H); 3.83 (t, J=5.2 Hz, 2H); 5.25 (broad s, 1H); 6.93 (dd, J=2.4, 6.8 Hz, 1H); 7.11-7.16 (m, 2H). MS (ESI): m/z=289.30 (M+H$^+$).

Example 33

4-(4-(2-Methoxyphenyl)piperazin-1-yl)butan-1-ol (21c) (Scheme 4) was synthesized from 17c according to the protocol described for 21a (Example 31). Colorless oil, 0.8 g (93%). $^1$H NMR (400 MHz, CDCl$_3$): δ 1.59-1.66 (m, 4H); 2.41-2.43 (m, 2H); 2.68 (broad s, 4H); 3.08 (broad s, 4H); 3.54-3.55 (m, 2H); 3.81 (s, 3H); 5.76 (broad s, 1H); 6.79-6.97 (m, 4H). MS (ESI): m/z=265.40 (M+H$^+$).

Example 34

4-(4-(2,3-Dichlorophenyl)piperazin-1-yl)butan-1-ol (21d) (Scheme 4) was synthesized from 17d according to the protocol described for 21a (Example 31). Colorless oil, 1.0 g (77%). $^1$H NMR (400 MHz, CDCl$_3$): δ 1.60-1.67 (m, 4H); 2.42-2.44 (m, 2H); 2.66 (broad s, 4H); 3.04 (broad s, 4H); 3.54-3.56 (m, 2H); 5.76 (broad s, 1H); 6.89-6.93 (m, 1H); 7.06-7.12 (m, 2H). MS (ESI): m/z=303.40 (M+H$^+$).

Example 35

3-(4-(2-Methoxyphenyl)piperazin-1-yl)propyl 2-oxo-1,2,3,4-tetrahydroquinoline-7-carboxylate 23a (Scheme 4)

A mixture of 2-oxo-1,2,3,4-tetrahydroquinoline-7-carboxylic acid (22) (0.43 g, 0.0022 mol), 3-(4-(methoxy-phenyl)piperazin-1-yl)propan-1-ol (21a) (0.6 g, 0.0022 mol), dicyclohexylcarbodiimide (0.45 g, 0.0022 mol), 4-(dimethylamino)pyridine (0.27 g, 0.0022 mol) in 15 mL THF was stirred at 40° C. for overnight (12 h). The progress of the reaction was monitored by thin layer chromatography (TLC). The reaction mixture was evaporated, the residue was diluted with DCM and filtered to remove urea, washed with DCM, the combined filtrate and washings were washed with saturated aqueous NaHCO$_3$ solution, dried over magnesium sulfate and evaporated to give the corresponding title compound 23a which was purified by silica gel chromatography using ethyl acetate. Off-white solid, 0.21 g (31%). $^1$H NMR (400 MHz, CDCl$_3$): δ 2.00 (quintet, 6.8 Hz, 2H); 2.58 (t, J=7.6 Hz, 2H); 2.65 (t, J=7.2 Hz, 2H); 2.67 (broad s, 4H); 3.02 (t, J=8.0 Hz, 2H); 3.09 (broad s, 4H); 3.85 (s, 3H); 4.39 (t, J=6.8 Hz, 2H); 6.84-7.01 (m, 4H); 7.22-7.27 (m, 1H); 7.44 (s, 1H); 7.66 (dd, J=1.6, 8.0 Hz, 1H); 8.26 (broad s, 1H). MS (ESI): m/z=424.20 (M+H$^+$).

Example 36

3-(4-(2,3-Dichlorophenyl)piperazin-1-yl)propyl 2-oxo-1, 2,3,4-tetrahydroquinoline-7-carboxylate (23b) (Scheme 4) was synthesized from the compound 21b and the carboxylic acid 22 according to the protocol described for the compound 23a (Example 35). White solid, 0.29 g (28%). $^1$H NMR (400 MHz, CDCl$_3$): δ 2.00 (quintet, 6.8 Hz, 2H); 2.59 (t, J=7.2 Hz, 2H); 2.66 (t, J=7.2 Hz, 2H); 2.68 (broad s, 4H); 3.02 (t, J=8.0 Hz, 2H); 3.06 (broad s, 4H); 4.41 (t, J=6.8 Hz, 2H); 6.93-6.95 (m, 1H); 7.11-7.16 (m, 2H); 7.23 (d, J=8.0 Hz, 1H); 7.46 (d, J=1.2 Hz, 1H); 7.67 (dd, J=1.6, 8.0 Hz, 1H); 8.32 (broad s, 1H). MS (ESI): m/z=462.10 (M+H$^+$).

Example 37

4-(4-(2-Methoxyphenyl)piperazin-1-yl)butyl 2-oxo-1,2,3,4-tetrahydroquinoline-7-carboxylate (23c) (Scheme 4) was synthesized from the compound 21c and the carboxylic acid 22 according to the protocol described for the compound 23a (Example 35). Off-white solid, 0.085 g (13%). $^1$H NMR (400 MHz, CDCl$_3$): δ 1.66-1.72 (m, 2H); 1.78-1.84 (m, 2H); 2.47 (t, J=7.6 Hz, 2H); 2.63-2.67 (m, 6H); 3.01 (t, J=7.2 Hz, 2H); 3.09 (broad s, 4H); 3.84 (s, 3H); 4.34 (t, J=6.8 Hz, 2H); 6.83-7.00 (m, 4H); 7.21 (d, J=8.0 Hz, 1H); 7.47 (s, 1H); 7.66 (dd, J=1.6, 8.0 Hz, 1H); 8.61 (broad s, 1H). MS (ESI): m/z=438.20 (M+H$^+$).

Example 38

4-(4-(2,3-Dichlorophenyl)piperazin-1-yl)butyl 2-oxo-1,2,3,4-tetrahydroquinoline-7-carboxylate (23d) (Scheme 4) was synthesized from the compound 21d and the carboxylic acid 22 according to the protocol described for the compound 23a (Example 35). White solid, 0.26 g (29%). $^1$H NMR (400 MHz, CDCl$_3$): δ 1.63-1.69 (m, 2H); 1.77-1.82 (m, 2H); 2.47 (t, J=7.6 Hz, 2H); 2.62-2.66 (m, 6H); 3.00 (t, J=7.2 Hz, 2H); 3.04 (broad s, 4H); 4.20 (t, J=5.6 Hz, 2H); 6.92 (dd, J=3.2, 6.4 Hz, 1H); 7.08-7.12 (m, 1H); 7.20 (d, J=8.0 Hz, 1H); 7.49-7.52 (m, 1H); 7.64 (dd, J=2.0, 8.0 Hz, 1H); 7.69 (dd, J=3.2, 6.0 Hz, 1H); 8.88 (broad s, 1H). MS (ESI): m/z=476.40 (M+H$^+$).

Example 39

3-(4-(2-Methoxyphenyl)piperazin-1-yl)propyl 2-oxo-1,2,3,4-tetrahydroquinoline-7-carboxylate hydrochloride (24a) (Scheme 4)

To a solution of the free base 23a (0.1 g) in 2 mL dichloromethane was added 4 mL 2M HCl solution in diethyl ether. The mixture was stirred at room temperature for 30 minutes. The solvent was evaporated, residue was triturated with ether, and solid precipitated was filtered, washed with ether and dried to give the corresponding hydrochloride 24a. The hydrochloride salt 24a gave satisfactory 1H NMR spectral data. White solid, 0.1 g (92%). MS (ESI): m/z=424.2 (M+H$^+$).

Example 40

3-(4-(2,3-Dichlorophenyl)piperazin-1-yl)propyl 2-oxo-1,2,3,4-tetrahydroquinoline-7-carboxylate hydrochloride (24b) (Scheme 4) was prepared from 23b according to the protocol described for the compound 24a (Example 39). The hydrochloride salt 24b gave satisfactory 1H NMR spectral data. White solid, 0.1 g (93%). MS (ESI): m/z=462.1 (M$^+$).

Example 41

4-(4-(2-Methoxyphenyl)piperazin-1-yl)butyl 2-oxo-1,2,3,4-tetrahydroquinoline-7-carboxylate hydrochloride (24c) (Scheme 4) was prepared from 23c according to the protocol described for the compound 24a (Example 39). The hydrochloride salt 24c gave satisfactory 1H NMR spectral data. Off-white solid, 0.04 g (43%). MS (ESI): m/z=438.2 (M+H$^+$).

Example 42

4-(4-(2,3-Dichlorophenyl)piperazin-1-yl)butyl 2-oxo-1,2,3,4-tetrahydroquinoline-7-carboxylate hydrochloride (24d) (Scheme 4) was prepared from the compound 23d according to the protocol described for the compound 24a (Example 39). The hydrochloride salt 24d gave satisfactory 1H NMR spectral data. White solid, 0.1 g (93%). MS (ESI): m/z=476.4 (M$^+$).

Example 43 tert-Butyl 4-(2-(4-ethoxy-4-oxobutoxy)phenyl)piperazine-1-carboxylate (13c) (Scheme 5) was synthesized from the compound 12 and 7b following the same protocol described for the compound 13a (Scheme 2, Example 13). Colorless oil, 1.6 g (99%). $^1$H NMR (400 MHz, CDCl$_3$): δ 1.21 (t, J=7.2 Hz, 3H); 1.46 (s, 9H); 2.13 (quintet, J=6.8 Hz, 2H); 2.51 (t, J=7.2 Hz, 2H); 2.98 (t, J=4.4 Hz, 4H); 3.57 (t, J=4.4 Hz, 4H); 4.02 (t, J=6.0 Hz, 2H); 4.11 (q, J=7.2 Hz, 2H); 6.82-6.97 (m, 4H). MS (ESI): m/z=393.50 (M+H$^+$).

Example 44

Ethyl 4-(2-(piperazin-1-yl)phenoxy)butanoate (25) (Scheme 5)

To a solution of tert-butyl 4-(2-(4-ethoxy-4-oxobutoxy) phenyl)piperazine-1-carboxylate 13c (0.5 g) in 1 mL DCM was added 1 mL trifluoroacetic acid. The resulting mixture was stirred at rt for 1 h. The color of the reaction mixture darkened and a gas was evolved. The progress of the reaction was monitored by thin layer chromatography (TLC). The reaction mixture was concentrated on rotavapor and the residue was poured onto a mixture of crushed ice and sodium bicarbonate (NaHCO$_3$). The aqueous layer was extracted with DCM, dried over magnesium sulfate and evaporated the solvent to give ethyl 4-(2-(piperazin-1-yl)phenoxy)butanoate 25. The compound 25 was carried to next step without any further purification. Brown oil, 0.37 g (99%). $^1$H NMR (400 MHz, CDCl$_3$): δ 1.22 (t, J=7.2 Hz, 3H); 2.13 (quintet, J=6.8 Hz, 2H); 2.51 (t, J=7.2 Hz, 2H); 3.08 (broad s, 8H); 4.02 (t, J=6.0 Hz, 2H); 4.11 (q, J=7.2 Hz, 2H); 6.82-6.97 (m, 4H). MS (ESI): m/z=293.50 (M+H$^+$).

Example 45

Ethyl 4-(2-(4-(3-hydroxypropyl)piperazin-1-yl)phenoxy)butanoate (27) (Scheme 5)

To a stirred solution of ethyl 4-(2-(piperazin-1-yl)phenoxy)butanoate 25 (0.48 g, 0.0016 mol) in 60 mL acetonitrile was added DIEA (0.56 mL, 0.0032 mol) followed by 3-bromo-1-propanol 26 (0.14 mL, 0.0016 mol) and the resulting mixture was stirred at 60° C. for 6 h. The progress of the reaction was monitored by thin layer chromatography (TLC). The reaction mixture was concentrated and the residue was diluted with DCM (50 mL). The reaction mixture was washed with water (50 mL×2), dried over magnesium sulfate and evaporated. The residue was purified by silica gel column chromatography using 0-100% gradient of hexane and ethyl acetate to give the pure ethyl 4-(2-(4-(3-hydroxypropyl)piperazin-1-yl)phenoxy)butanoate 27. Brown oil, 0.39 g (63%).

¹H NMR (400 MHz, CDCl₃): δ 1.21 (t, J=7.2 Hz, 3H); 2.00 (quintet, J=7.2 Hz, 2H); 2.13 (quintet, J=7.2 Hz, 2H); 2.51 (t, J=7.2 Hz, 2H); 3.08 (broad s, 8H); 3.54 (t, J=6.4 Hz, 2H); 4.02 (t, J=6.4 Hz, 2H); 4.11 (q, J=7.2 Hz, 2H); 4.13-4.18 (m, 2H); 6.83-7.25 (m, 4H). MS (ESI): m/z=351.50 (M+H⁺).

Example 46

3-(4-(2-(4-ethoxy-4-oxobutoxy)phenyl)piperazin-1-yl)propyl 2-oxo-1,2,3,4-tetrahydroquinoline-7-carboxylate (28) (Scheme 5)

A mixture of 2-oxo-1,2,3,4-tetrahydroquinoline-7-carboxylic acid 22 (0.21 g, 0.001 mol), ethyl 4-(2-(4-(3-hydroxypropyl)piperazin-1-yl)phenoxy)butanoate 27 (0.38 g, 0.001 mol), dicyclohexylcarbodiimide (0.21 g, 0.001 mol), 4-(dimethylamino)pyridine (0.12 g, 0.001 mol) in 20 mL THF was stirred at room temperature for 12 hours. The progress of the reaction was monitored by thin layer chromatography (TLC). The reaction mixture was evaporated; the residue was diluted with DCM (25 mL). The filtrate was washed with saturated aqueous NaHCO₃ solution (25 mL×2) and water (25 mL×2), dried over sodium sulfate (Na₂SO₄) and evaporated. The residue was purified by silica gel column chromatography using 0-100% gradient of hexane and ethyl acetate to give the pure 3-(4-(2-(4-ethoxy-4-oxobutoxy)phenyl)piperazin-1-yl)propyl 2-oxo-1,2,3,4-tetrahydroquinoline-7-carboxylate 28. Colorless oil, 0.075 g (13%). ¹H NMR (400 MHz, CDCl₃): δ 1.21 (t, J=7.2 Hz, 3H); 1.99 (quintet, J=7.2 Hz, 2H); 2.13 (quintet, J=7.2 Hz, 2H); 2.50-2.65 (m, 8H); 2.99 (t, J=7.6 Hz, 4H); 3.08 (broad s, 4H); 4.01 (t, J=6.4 Hz, 2H); 4.12 (q, J=7.2 Hz, 2H); 4.38 (t, J=6.4 Hz, 2H); 6.81-6.89 (m, 4H); 7.20 (d, J=8.0 Hz, 1H); 7.50 (d, J=1.6 Hz, 1H); 7.64 (dd, J=1.6, 8.0 Hz, 1H, 9.00 (broad s, 1H). MS (ESI): m/z=524.50 (M+H⁺).

Example 47

Ethyl 3-(tert-butoxycarbonylamino)propanoate (30) (Scheme 6)

To a stirred suspension of β-alanine ethyl ester hydrochloride (29) (2 g, 0.01 mol) in 20 mL THF at ice-bath temperature was added triethylamine (2.8 mL, 0.02 mol) followed by a solution of di-tert-butylcarbonate (11) (2.62 g, 0.012 mol) in 10 mL THF at room temperature. The resulting mixture was heated at 60° C. for 6 h. The reaction mixture was filtered (to remove triethylamine hydrochloride salt) and the filtrate was concentrated on rotavapor. The residue was dissolved in ethyl acetate (50 mL), washed with water (25 mL×2), dried (Na₂SO₄) and evaporated to give the pure compound 30. Colorless oil (2.8 g, 99%). ¹H NMR (400 MHz, CDCl₃): δ 1.19 (t, J=7.2 Hz, 3H); 1.36 (s, 9H); 2.43 (t, J=6.4 Hz, 2H); 3.48 (t, J=6.4 Hz, 2H); 4.07 (q, J=7.2 Hz, 2H). MS (ESI): m/z=218.4 (M+H⁺).

Example 48 tert-Butyl 3-hydroxypropylcarbamate (31) (Scheme 6) was prepared from the compound 30 according to the protocol described for the compound 21a (Scheme 4, Example 31). Colorless oil (2.03 g, 90%). ¹H NMR (400 MHz, CDCl₃): δ 1.36 (s, 9H); 1.59 (quintet, J=6.0 Hz, 2H); 3.17-3.22 (m, 2H); 3.52-3.57 (m, 2H); 4.90 (broad s, 1H). MS (ESI): m/z=176.3 (M+H⁺).

Example 49

3-(tert-butoxycarbonylamino)propyl 4-methylbenzenesulfonate (32) (Scheme 6)

To a stirred solution of tert-butyl-3-hydroxypropylcarbamate 31 (2.03 g, 0.008 mol) in 20 mL dichloromethane at ice-bath temperature was added p-toluenesulfonyl chloride (2.34 g, 0.012 mol) followed by pyridine (0.97 mL, 0.012 mol). The resulting mixture was stirred at 0° C. for 6 h. The progress of the reaction was monitored by thin layer chromatography (TLC). The reaction mixture was diluted with dichloromethane (50 mL), washed with saturated aqueous sodium bicarbonate solution (25 mL×2), water (25 mL), dried (Na₂SO₄) and evaporated. The residue was purified by silica gel column chromatography using a gradient of hexane and ethyl acetate to give the pure compound 32. Colorless oil (2.2 g, 57%). ¹H NMR (400 MHz, CDCl₃): δ 1.37 (s, 9H); 1.80 (quintet, J=6.0 Hz, 2H); 2.40 (s, 3H); 3.08-3.18 (m, 2H); 4.00-4.07 (m, 2H); 7.30-7.32 (m, 2H); 7.75 (dd, J=8.4, 2.0 Hz, 2H). MS (ESI): m/z=230.3 (M+H⁺-ᵗBuCO₂).

Example 50 tert-Butyl 3-(4-(2-methoxyphenyl)piperazin-1-yl) propylcarbamate (33) (Scheme 6)

To a solution of 3-(tert-butoxycarbonylamino)propyl 4-methylbenzenesulfonate (32) (0.5 g, 0.0015 mol) in 10 mL anhydrous DMF at ice-bath temperature was added DIEA (0.8 mL, 0.0045 mol) followed by 1-(2-methoxyphenyl)piperazine hydrochloride (4) (0.35 g, 0.0015 mol). The resulting mixture was allowed to reach room temperature and then heated to 80° C. for overnight (12 h). The progress of the reaction was monitored by thin layer chromatography (TLC). The reaction mixture was diluted with ethyl acetate (25 mL), washed with saturated aqueous sodium bicarbonate solution (25 mL), water (25 mL) dried (Na₂SO₄) and evaporated. The residue was purified by silica gel column chromatography using 0-100% gradient of hexane and ethyl acetate to give the pure compound 33. Colorless oil (0.3 g, 57%). ¹H NMR (400 MHz, CDCl₃): δ 1.42 (s, 9H); 1.68 (quintet, J=6.8 Hz, 2H); 2.47 (t, J=6.8 Hz, 2H); 2.48 (broad s, 4H); 3.07 (broad s, 4H); 3.50-3.54 (m, 2H); 3.83 (s, 3H); 6.83-7.04 (m, 4H). MS (ESI): m/z=350.5 (M+H⁺).

Example 51

3-(4-(2-Methoxyphenyl)piperazin-1-yl)propan-1-amine (34) (Scheme 6) was prepared from the compound 33 according to the protocol described for the intermediate in the preparation of compound 14a (Scheme 2, Example 15). Colorless oil (0.25 g, 90%). MS (ESI): m/z=250.4 (M+H⁺).

Example 52

N-(3-(4-(2-methoxyphenyl)piperazin-1-yl)propyl)-2-oxo-1,2,3,4-tetrahydroquinoline-7-carboxamide (35) (Scheme 6) was prepared from 3-(4-(2-methoxyphenyl)piperazin-1-yl)propan-1-amine (34) and 2-oxo-1,2,3,4-tetrahydroquinoline-7-carboxylic acid (22) according to the protocol described for the compound 23 (Scheme 4, Example 35). Colorless oil (0.1 g, 20%). ¹H NMR (400 MHz, CDCl₃): δ 1.67 (quintet, J=6.4 Hz, 2H); 1.73-1.78 (m, 2H); 2.62 (t, J=8.0 Hz, 2H); 2.70 (broad s, 4H); 3.05-3.08 (m, 5H); 3.47-3.49 (m, 2H); 3.85 (s, 3H); 4.21 (t, J=5.6 Hz, 2H); 6.86 (d, J=7.6 Hz, 1H); 6.92-6.95 (m, 2H); 6.98-7.03 (m, 1H); 7.35 (d, J=1.2 Hz, 1H); 7.52 (dd, J=6.0, 3.6 Hz, 1H); 7.70 (dd, J=6.0, 3.6 Hz, 1H). MS (ESI): m/z=404.5 (M$^+$–H$_2$O).

Example 53

Ethyl 2-oxo-1,2,3,4-tetrahydroquinoline-7-carboxylate (36) (Scheme 7)

To a suspension of 2-oxo-1,2,3,4-tetrahydroquinoline-7-carboxylic acid (22) (6 g, 1 mol) in 120 mL anhydrous ethanol was added 1.2 mL concentrated sulfuric acid at room temperature. The resulting mixture was stirred at reflux for 48 h (until the suspension became a clear solution). The solvent was evaporated. The residue was diluted with dichloromethane and washed with saturated aqueous NaHCO$_3$ solution, dried (MgSO$_4$) and evaporated. The residue was triturated with MTBE and filtered to give the pure carboxylate 36. White solid, 5.7 g (83%). $^1$H NMR (400 MHz, CDCl$_3$): δ 1.38 (t, J=7.2 Hz, 3H); 2.66 (t, J=8.0 Hz, 2H); 3.02 (t, J=8.0 Hz, 2H); 4.37 (q, J=7.2 Hz, 2H); 7.22 (d, J=8.0 Hz, 1H); 7.48 (s, 1H); 7.67 (dd, J=1.6, 8.0 Hz, 1H); 8.59 (broad s, 1H). MS (ESI): m/z=220.30 (M+H$^+$).

Example 54

7-(Hydroxymethyl)-3,4-dihydroquinolin-2(1H)-one (37) (Scheme 7)

A mixture of ethyl 2-oxo-1,2,3,4-tetrahydroquinoline-7-carboxylate (36) (4.8 g, 0.022 mol) and sodium borohydride (12.5 g, 0.039 mol) in 250 mL ethanol was refluxed for overnight. The progress of the reaction was monitored by thin layer chromatography (TLC). The reaction mixture was evaporated; the residue was diluted with DCM, washed with saturated aqueous NaHCO$_3$ solution (25 mL×2) and water (25 mL×2), dried (Na$_2$SO$_4$) and evaporated under reduced pressure. The residue was purified by silica gel column chromatography using 0-100% gradient of hexane and ethyl acetate to give the pure hydroxymethyl quinolinone 37. White solid, 0.85 g (22%). $^1$H NMR (400 MHz, CDCl$_3$): δ 2.40 (t, J=7.6 Hz, 2H); 2.81 (t, J=7.2 Hz, 2H); 4.38 (d, J=5.6 Hz, 2H); 5.11 (t, J=5.6 Hz, 1H); 6.80-6.82 (m, 2H); 7.06 (d, J=8.0 Hz, 1H), 10.04 (s, 1H). MS (ESI): m/z=178.30 (M+H$^+$).

Example 55

(2-Oxo-1,2,3,4-tetrahydroquinolin-7-yl)methyl 3-(4-(2-methoxyphenyl)piperazin-1-yl)propanoate (38a) (Scheme 7)

A mixture of 7-(hydroxymethyl)-3,4-dihydroquinolin-2 (1H)-one (37) (0.15 g, 0.0008 mol), the carboxylic acid 18a (0.001 mol), dicyclohexylcarbodiimide (0.2 g, 0.001 mol), 4-(dimethylamino)pyridine (0.12 g, 0.001 mol) in 15 mL THF was stirred at 40° C. for overnight (12 h). The progress of the reaction was monitored by thin layer chromatography (TLC). The reaction mixture was evaporated; the residue was diluted with DCM, filtered to remove the urea precipitated, washed with saturated aqueous NaHCO$_3$ solution (25 mL) and water (25 mL×2), dried (Na$_2$SO$_4$) and evaporated under reduced pressure to give the corresponding title compound 38a which was purified by silica gel column chromatography using 0-100% gradient of hexane and ethyl acetate. Colorless oil, 0.064 g (18%). $^1$H NMR (400 MHz, CDCl$_3$): δ 2.55-2.60 (m, 4H); 2.64 (broad s, 4H); 2.76 (t, J=7.6 Hz, 2H); 2.93 (t, J=7.6 Hz, 2H); 3.02 (broad s, 4H); 3.72 (s, 3H); 5.05 (s, 2H); 6.81-6.84 (m, 2H); 6.88-6.90 (m, 2H); 6.95-6.98 (m, 2H); 7.07-7.12 (m, 1H); 9.14 (s, 1H). MS (ESI): m/z=423.50 (M+H$^+$).

Example 56

(2-Oxo-1,2,3,4-tetrahydroquinolin-7-yl)methyl 3-(4-(2,3-dichlorophenyl)piperazin-1-yl)propanoate (38b) (Scheme 7) was prepared from the carbinol 37 and the carboxylic acid 18b according to the protocol described for the compound 38a (Example 55). Colorless oil, 0.39 g (99%). $^1$H NMR (400 MHz, CDCl$_3$): δ 2.55-2.60 (m, 4H); 2.62 (broad s, 4H); 2.78 (t, J=7.6 Hz, 2H); 2.93 (t, J=7.6 Hz, 2H); 3.00 (broad s, 4H); 5.05 (s, 2H); 6.83 (s, 1H); 6.90-6.93 (m, 1H); 6.98 (dd, J=1.2, 7.6 Hz, 1H); 7.09-7.13 (m, 3H); 9.22 (broad s, 1H). MS (ESI): m/z=462.10 (M+H$^+$).

Example 57

(2-Oxo-1,2,3,4-tetrahydroquinolin-7-yl)methyl 4-(4-(2-methoxyphenyl)piperazin-1-yl)butanoate (38c) (Scheme 7) was prepared from the carbinol 37 and the carboxylic acid 18c according to the protocol described for the compound 38a (Example 55). Colorless oil, 0.15 g (41%). $^1$H NMR (400 MHz, CDCl$_3$): δ 1.84 (quintet, J=7.2 Hz, 2H); 2.38-2.54 (m, 4H); 2.58-2.60 (m, 6H); 2.95 (t, J=8.4 Hz, 2H); 3.03 (broad s, 4H); 3.80 (s, 3H); 5.02 (s, 2H); 6.80-6.94 (m, 4H); 7.09 (d, J=7.6 Hz, 1H); 9.30 (m, 1H). MS (ESI): m/z=438.20 (M+H$^+$).

Example 58

(2-Oxo-1,2,3,4-tetrahydroquinolin-7-yl)methyl 4-(4-(2,3-dichlorophenyl)piperazin-1-yl)butanoate (38d) (Scheme 7) was prepared from the carbinol 37 and the carboxylic acid 18d according to the protocol described for the compound 38a (Example 55). White solid, 0.2 g (50%). $^1$H NMR (400 MHz, CDCl$_3$): δ 1.85 (quintet, J=7.2 Hz, 2H); 2.39-2.42 (m, 4H); 2.59-2.63 (m, 6H); 2.94 (t, J=8.4 Hz, 2H); 3.01 (broad s, 4H); 5.04 (s, 2H); 6.83 (d, J=1.6 Hz, 1H); 6.90-6.93 (m, 1H); 6.96 (dd, J=1.2, 7.6 Hz, 1H); 6.97-7.13 (m, 3H); 9.29 (s, 1H). MS (ESI): m/z=476.10 (M+H$^+$).

Example 59

(2-Oxo-1,2,3,4-tetrahydroquinolin-7-yl)methyl 3-(4-(2-methoxyphenyl)piperazin-1-yl)-propanoate hydrochloride (39a) (Scheme 7)

To a solution of the free base 38a (0.1 g) in 2 mL dichloromethane was added 4 mL 2M HCl solution in diethyl ether. The mixture was stirred at room temperature for 30 minutes. The solvent was evaporated, residue was triturated with ether, and solid precipitated was filtered, washed with ether and air dried to give the corresponding hydrochloride 39a. The hydrochloride salt 39a gave satisfactory 1H NMR spectral data. Off-white solid, 0.03 g (43%). MS (ESI): m/z=423.5 (M$^-$).

Example 60

(2-Oxo-1,2,3,4-tetrahydroquinolin-7-yl)methyl 3-(4-(2,3-dichlorophenyl)piperazin-1-yl)propanoate hydrochloride (39b) (Scheme 7) was prepared from the compound 38b according to the protocol described for the compound 39a (Example 59). The hydrochloride salt 39b gave satisfactory 1H NMR spectral data. White solid, 0.4 g (93%). MS (ESI): m/z=462.1 (M$^+$).

Example 61

(2-Oxo-1,2,3,4-tetrahydroquinolin-7-yl)methyl 4-(4-(2-methoxyphenyl)piperazin-1-yl)butanoate hydrochloride (39c) (Scheme 7) was prepared from the compound 38c according to the protocol described for the compound 39a (Example 49). The hydrochloride salt 39c gave satisfactory 1H NMR spectral data. White solid, 0.05 g (31%). MS (ESI): m/z=438.2 (M+H$^+$).

Example 62

(2-Oxo-1,2,3,4-tetrahydroquinolin-7-yl)methyl 4-(4-(2,3-dichlorophenyl)piperazin-1-yl)butanoate (39d) (Scheme 7) was prepared from the compound 38d according to the protocol described for the compound 39a (Example 49). The hydrochloride salt 39d gave satisfactory 1H NMR spectral data. White solid, 0.1 g (93%). MS (ESI): m/z=476.1 (M$^+$).

Example 63

3-(4-(2-Methoxyphenyl)piperazin-1-yl)propyl methanesulfonate (40) (Scheme 8)

To a stirred solution of 3-(4-(2-methoxyphenyl)piperazin-1-yl)propan-1-ol 21 (0.1 g, 0.0004 mol) and 0.1 mL of triethylamine in 10 mL of anhydrous dichloromethane at ice-bath temperature was added methanesulfonyl chloride (0.034 mL, 0.00044 mol) dropwise. The resulting mixture was allowed to warm to room temperature slowly and stirred there for 3 h. The progress of the reaction was monitored by thin layer chromatography. The reaction mixture was diluted with 50 mL of water, washed with saturated aqueous sodium bicarbonate solution (25 mL×2) followed by brine (25 mL×2), dried over sodium sulfate ($Na_2SO_4$) and evaporated. The residue was purified by a short silica gel column chromatography using 0-100% gradient of hexane and ethyl acetate to give the pure compound 40. Colorless oil (0.1 g, 76%). $^1$H NMR (400 MHz, $CDCl_3$): δ 1.65 (quintet, J=6.4 Hz, 2H); 3.05 (s, 3H); 3.10-3.20 (broad s, 4H); 3.30-3.40 (broad s, 4H); 3.83 (s, 3H); 4.18 (t, J=6.0 Hz, 2H); 4.38 (t, J=6.0 Hz, 2H); 6.83-6.91 (m, 3H); 6.99-7.04 (m, 1H). MS (ESI): m/z=329.4 (M+H$^+$).

Example 64

7-((3-(4-(2-Methoxyphenyl)piperazin-1-yl)propoxy)methyl)-3,4-dihydroquinolin-2(1H)-one (41) (Scheme 8)

To a stirred suspension of sodium hydride (0.019 g, 0.0004 mol) in 5 mL of anhydrous THF was added a solution of 3-(4-(2-methoxyphenyl)piperazin-1-yl)propyl methanesulfonate (40) (0.13 g, 0.0004 mol) in 5 mL THF at ice-bath temperature followed by 7-(hydroxymethyl)-3,4-dihydroquinolin-2(1H)-one (37) (0.07 g, 0.0004 mol) in 5 mL THF dropwise. After the completion of the addition, the resulting reaction mixture was allowed to warm up to room temperature and stirred at 50° C. for 6 h. The progress of the reaction was monitored by thin layer chromatography (TLC). The reaction mixture was evaporated, diluted with 50 mL ethyl acetate, washed with saturated aqueous $NaHCO_3$ solution (25 mL) followed by brine (25 mL), dried ($Na_2SO_4$) and evaporated. The residue was purified by silica gel column chromatography using 0-100% gradient of hexane and ethyl acetate to give the pure compound 41. Colorless oil (0.1 g, 62%). $^1$H NMR (400 MHz, $CDCl_3$): δ 1.88 (quintet, J=6.8 Hz, 2H); 2.50 (t, J=7.6 Hz, 2H); 2.59 (t, J=7.6 Hz, 2H); 2.66 (broad s, 4H); 2.84 (t, J=7.6 Hz, 2H); 3.06 (broad s, 4H); 3.83 (s, 3H); 3.98 (t, J=7.6 Hz, 2H); 4.63 (s, 2H); 6.82-6.84 (m, 2H); 6.88-6.99 (m, 4H); 7.08-7.10 (m, 2H). MS (ESI): m/z=410.5 (M+H$^+$).

Example 65

4-Bromo-3-nitrobenzoic acid (43) (Scheme 9)

Fuming nitric acid (12.4 mL, 0.3 mol) was slowly added to conc. sulfuric acid (30.1 mL, 0.6 mol) at 0-5° C. The cooled nitrating mixture was taken in a beaker equipped with a mechanical stirrer and addition funnel. 4-Bromotoluic acid 42 (40 g, 0.2 mol) was added to this mixture in small portions over 5 hours at such a rate to maintain the temperature at 0-5° C. The reaction mixture was stirred further for additional 2 h at room temperature and then poured over ice. The solid that separated was filtered, washed with water till it was free of acid and then air dried to constant weight to give the pure compound 43. White solid (47.2 g, 96%). $^1$H NMR (300 MHz, $CDCl_3$): δ 7.85 (d, J=12.0 Hz, 1H); 8.09 (d, J=12.0 Hz, 1H); 8.48 (s, 1H). $^{13}$C NMR (75 MHz, $CDCl_3$): δ 124.2, 132.1, 135.2, 138.0, 139.8, 159.8, 171.0.

Example 66

4-(3-Ethoxy-3-oxoprop-1-enyl)-3-nitrobenzoic acid (45) (Scheme 9)

To 4-bromo-3-nitrobenzoic acid (43) (30 g, 0.12 mol), palladium(II) acetate (1.1 g, 49 mmol) and triphenylphosphine (1.27 g, 49 mmol) in 100 mL DMF were added triethyl amine (25.2 mL, 0.2 mol) and ethyl acrylate (44) (20 mL, 0.2 mol). The reaction was stirred at 110° C. for 12 h, cooled to room temperature, and poured into a separatory funnel containing toluene (150 mL). The mixture was washed with 1N HCl (100 mL) and water (2×150 mL). The organic extracts were concentrated to give the pure compound 45. White solid (29.5 g, 92%). $^1$H NMR (300 MHz, $CDCl_3$): δ 1.35 (t, J=7.2 Hz, 3H); 4.30 (q, J=7.2 Hz, 2H); 6.45 (d, J=14.4 Hz, 1H); 7.80 (d, J=8.4 Hz, 1H); 8.15 (d, J=14.4 Hz, 1H); 8.35 (d, J=8.4 Hz, 1H); 8.75 (s, 1H). $^{13}$C NMR (75 MHz, $CDCl_3$): δ 14.5, 62.0, 125.5, 126.0, 129.0, 131.2, 134.2, 135.4, 139.0, 148.2, 165.5, 169.0.

Example 67

2-Oxo-1,2,3,4-tetrahydroquinoline-7-carboxylic acid (22) (Scheme 9)

To 10% Pd—C (100 mg) under nitrogen atmosphere was added a solution of 4-(3-ethoxy-3-oxoprop-1-enyl)-3-nitrobenzoic acid (45) (29 g, 0.11 mol) in 75 mL methanol and kept at 50 psi $H_2$ atmosphere for 12 h. The reaction mixture was filtered through a sintered funnel and the filtrate was concentrated to give the pure compound 22. Off-white solid (20.9 g, 96%). $^1$H NMR (400 MHz, $CDCl_3$): δ 2.44 (t, J=6.8 Hz, 2H); 2.90 (t, J=6.8 Hz, 2H); 7.25 (d, J=7.6 Hz, 1H); 7.44 (s, 1H); 7.47 (dd, J=7.6, 1.6 Hz, 1H); 10.22 (broad s, 1H); 12.85 (broad s, 1H). $^{13}$C NMR (75 MHz, $CDCl_3$): δ 24.8, 30.0, 115.1, 123.5, 127.8, 127.9, 129.0, 139.0, 167.5, 169.0.

Example 68

In Vitro Pharmacology Results

The quinolinone derivatives comprising Formulae (I)-(X) described in this invention and synthesized above were tested using in vitro pharmacological assays to evaluate their activities for dopamine, $D_{2S}$, serotonin, $5\text{-HT}_{1A}$ and serotonin, $5\text{-HT}_{2A}$ receptors. The in vitro assay protocols and literature references are described herein.

| Dopamine, $D_{2S}$ (human recombinant) binding assay: Materials and Methods: | |
|---|---|
| Receptor Source: | Human recombinant expressed in CHO cells |
| Radioligand: | [$^3$H]Spiperone (20-60 Ci/mmol) |
| Control Compound: | Haloperidol |
| Incubation Conditions: | |

The reactions were carried out in 50 mM TRIS-HCl (pH 7.4) containing 120 mM NaCl, 5 mM KCl, 5 mM MgCl$_2$, 1 mM EDTA for 60 minutes at 25 C. The reaction was terminated by rapid vacuum filtration onto glass fiber filters. Radioactivity trapped onto the filters was determined and compared to control values in order to ascertain any interactions of test compounds with the cloned dopamine-D$_2$ short binding site (Literature Reference: Jarvis, K. R. et al. Journal of Receptor Research 1993, 13(1-4), 573-590; Gundlach, A. L. et al. Life Sciences 1984, 35, 1981-1988.)

| Serotonin, $5HT_{1A}$ (human recombinant) binding assay: Materials and Methods: | |
|---|---|
| Receptor Source: | Human recombinant expressed in HEK-293 cells |
| Radioligand: | [$^3$H]-8-OH-DPAT (221 Ci/mmol) |
| Control Compound: | 8-OH-DPAT |
| Incubation Conditions: | |

The reactions were carried out in 50 mM TRIS-HCl (pH 7.4) containing 10 mM MgSO$_4$, 0.5 mM EDTA and 0.1% Ascorbic acid at room temperature for 1 hour. The reaction was terminated by rapid vacuum filtration onto glass fiber filters. Radioactivity trapped onto the filters was determined and compared to control values in order to ascertain any interactions of test compounds with the cloned serotonin-$5HT_{1A}$ binding site (Literature Reference: Hoyer, D. et al. Eur. Journal Pharmacol. 1985, 118, 13-23; Schoeffter, P. and Hoyer, D. Naunyn-Schmiedeberg's Arch. Pharmac. 1989, 340, 135-138)

| Serotonin, $5HT_{2A}$ (human) binding assay: Materials and Methods: | |
|---|---|
| Receptor Source: | Human Cortex |
| Radioligand: | [$^3$H]-Ketanserin (60-90 Ci/mmol) |
| Control Compound: | Ketanserin |
| Incubation Conditions: | |

The reactions were carried out in 50 mM TRIS-HCl (pH 7.6) at room temperature for 90 minutes. The reaction was terminated by rapid vacuum filtration onto glass fiber filters. Radioactivity trapped onto the filters was determined and compared to control values in order to ascertain any interactions of test compounds with the serotonin-$5HT_{2A}$ binding site (Literature Reference: Leysen, J. E. et al. Mol. Pharmacol. 1982, 21, 301-314; Martin, G. R. and Humphrey, P. P. A. Neuropharmacol. 1994, 33(3/4), 261-273.)

The radioligand binding assays for dopamine-$D_{2S}$ and serotonin-$5HT_{1A}$ were carried out at six different concentrations and the test concentrations were 1 nM, 5 nM, 10 nm 50 nM, 100 nM and 500 nM. The radioligand binding assays for serotonin-$5HT_{2A}$ were carried out at seven different concentrations and the test concentrations were 5 nM, 10 nM, 50 nM, 100 nM, 500 nM, 1 uM, and 300 uM.

The in vitro pharmacological activities of the selected compounds using radioligand binding assays are reported in the following table.

| Compound | Assay | IC50 | Ki |
|---|---|---|---|
| 9a (Example 8) | D2S | 5.83 nM | 1.69 nM |
| 9a (Example 8) | 5-HT1A | 6.61 nM | 3.93 nM |
| 9a (Example 8) | 5-HT2A | 456 nM | 239 nM |
| 39d (Example 62) | D2S | 54.70 nM | 12.80 nM |
| 39d (Example 62) | 5-HT1A | 85 nM | 48.50 nM |
| 39d (Example 62) | 5-HT2A | 313 nM | 171 nM |
| 24b (Example 40) | D2S | 72.90 nM | 17 nM |
| 24b (Example 40) | 5-HT1A | 28 nM | 16 nM |
| 24b (Example 40) | 5-HT2A | 253 nM | 147 nM |

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference.

What is claimed is:

1. A compound having structural Formula (II):

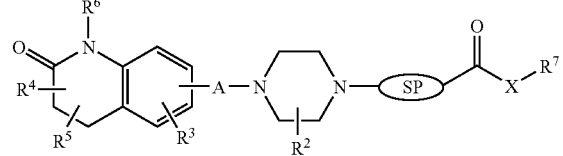

Formula II or a pharmaceutically acceptable salt thereof, wherein
X is O, S, NH or NR$^8$;
SP is a spacer selected from the group consisting of O, S, alkyl, substituted alkyl, acylamino, alkoxy, alkylamino, alkylthio, or aryloxyalkyl;
A is —O—(CH$_2$)$_n$—, wherein n is an integer between 1 and 7;
R$^2$, R$^3$, R$^4$, R$^5$ and R$^6$ are independently selected from the group consisting of hydrogen, alkyl, substituted alkyl, aryl, substituted aryl, arylalkyl, substituted arylalkyl, cycloalkyl, substituted cycloalkyl, alkoxy, alkylsulfinyl, alkylsulfonyl, alkylthio, amino, alkylamino, arylalkylamino, dialkylamino, arylalkoxy, cyano, halogen, or hydroxy, wherein R$^4$ and R$^5$ are optionally present on the same carbon;
R$^7$ is alkyl, substituted alkyl, aryl, substituted aryl, arylalkyl, substituted arylalkyl, cycloalkyl, or substituted cycloalkyl; and
R$^8$ is alkyl, or substituted alkyl.

2. The compound of claim 1, wherein the spacer is aryloxyalkyl.

3. The compound of claim 2, wherein the spacer is alky or substituted alkyl.

4. A compound having structural Formula (III):

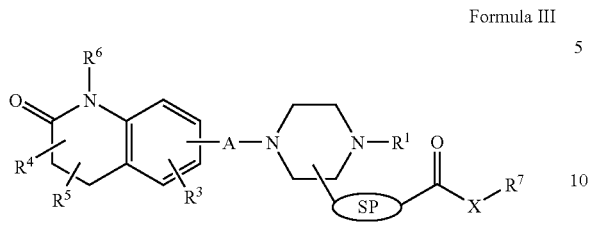

Formula III or a pharmaceutically acceptable salt, hydrate or solvate thereof, wherein X is O, S, NH or $NR^8$;
SP is a spacer selected from the group consisting of O, S, alkyl, substituted alkyl, acylamino, alkoxy, alkylamino, alkylthio, or aryloxyalkyl;
A is $-O-(CH_2)_n-$, wherein n is an integer between 1 and 7;
$R^1$, $R^3$, $R^4$, $R^5$ and $R^6$ are independently selected from the group consisting of hydrogen, alkyl, substituted alkyl, aryl, substituted aryl, arylalkyl, substituted arylalkyl, cycloalkyl, substituted cycloalkyl, alkoxy, alkylsulfinyl, alkylsulfonyl, alkylthio, amino, alkylamino, arylalkylamino, dialkylamino, arylalkoxy, cyano, halogen, or hydroxy, wherein $R^4$ and $R^5$ are optionally present on the same carbon;
$R^7$ is alkyl, substituted alkyl, aryl, substituted aryl, arylalkyl, substituted arylalkyl, cycloalkyl, or substituted cycloalkyl; and
$R^8$ is alkyl, or substituted alkyl.

5. A compound having structural Formula (IV):

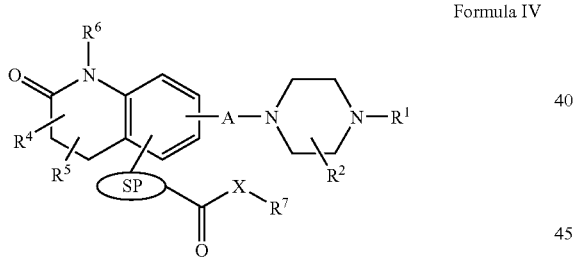

Formula IV or a pharmaceutically acceptable salt, hydrate or solvate thereof, wherein X can be O, S, NH or $NR^8$;
SP is a spacer selected from the group consisting of O, S, alkyl, substituted alkyl, acylamino, alkoxy, alkylamino, alkylthio, or aryloxyalkyl;
A is $-O-(CH_2)_n-$, wherein n is an integer between 1 and 7;
$R^1$, $R^2$, $R^4$, $R^5$, and $R^6$ are independently selected from the group consisting of hydrogen, alkyl, substituted alkyl, aryl, substituted aryl, arylalkyl, substituted arylalkyl, cycloalkyl, substituted cycloalkyl, alkoxy, alkylsulfinyl, alkylsulfonyl, alkylthio, amino, alkylamino, arylalkylamino, dialkylamino, arylalkoxy, cyano, halogen, or hydroxy, wherein $R^4$ and $R^5$ are optionally present on the same carbon;
$R^7$ is alkyl, substituted alkyl, aryl, substituted aryl, arylalkyl, substituted arylalkyl, cycloalkyl, or substituted cycloalkyl; and
$R^8$ is alkyl, or substituted alkyl.

6. A compound having structural Formula (V):

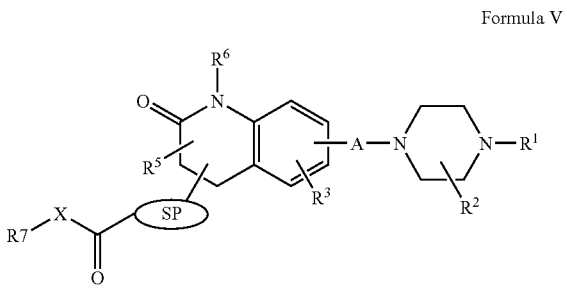

Formula V or a pharmaceutically acceptable salt, hydrate or solvate thereof, wherein X is O, S, NH or $NR^8$;
SP is a spacer selected from the group consisting of O, S, alkyl, substituted alkyl, acylamino, alkoxy, alkylamino, alkylthio, or aryloxyalkyl;
A s $-O-(CH_2)_n-$, wherein n is an integer between 1 and 7;
$R^1$, $R^2$, $R^3$, $R^5$ and $R^6$ are independently selected from the group consisting of hydrogen, alkyl, substituted alkyl, aryl, substituted aryl, arylalkyl, substituted arylalkyl, cycloalkyl, substituted cycloalkyl, alkoxy, alkylsulfinyl, alkylsulfonyl, alkylthio, amino, alkylamino, arylalkylamino, dialkylamino, arylalkoxy, cyano, halogen, or hydroxy;
$R^7$ is alkyl, substituted alkyl, aryl, substituted aryl, arylalkyl, substituted arylalkyl, cycloalkyl, or substituted cycloalkyl; and
$R^8$ is alkyl, or substituted alkyl.

7. A compound having structural Formula (VI):

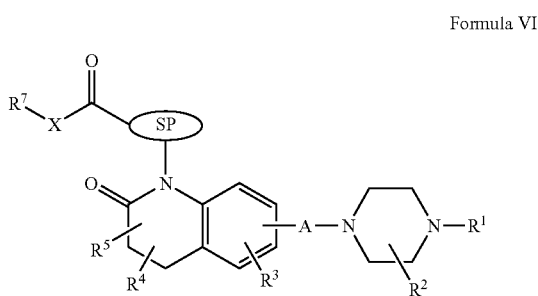

Formula VI or a pharmaceutically acceptable salt, hydrate or solvate thereof,
wherein X is O, S, NH or $NR^8$;
SP is a spacer selected from the group consisting of O, S, alkyl, substituted alkyl, acylamino, alkoxy, alkylamino, alkylthio, or aryloxyalkyl;
A is $-O-(CH_2)_n-$, wherein n is an integer between 1 and 7;
$R^1$, $R^2$, $R^3$, $R^4$ and $R^5$ are independently selected from the group consisting of hydrogen, alkyl, substituted alkyl, aryl, substituted aryl, arylalkyl, substituted arylalkyl, cycloalkyl, substituted cycloalkyl, alkoxy, alkylsulfinyl, alkylsulfonyl, alkylthio, amino, alkylamino, arylalkylamino, dialkylamino, arylalkoxy, cyano, halogen, or hydroxy, wherein $R^4$ and $R^5$ are optionally present on the same carbon;
$R^7$ is alkyl, substituted alkyl, aryl, substituted aryl, arylalkyl, substituted arylalkyl, cycloalkyl, or substituted cycloalkyl; and
$R^8$ is alkyl, or substituted alkyl.

8. The compound of claim 1 having structural Formula (VII):

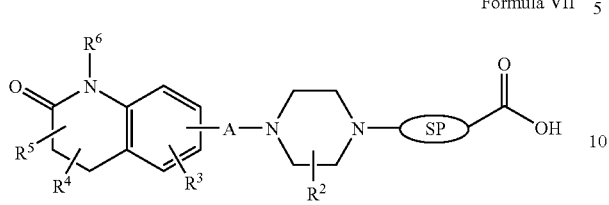

Formula VII or a pharmaceutically acceptable salt, hydrate or solvate thereof.

9. The compound of claim 4 having structural Formula (VIII):

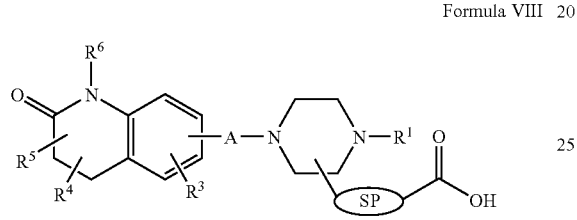

Formula VIII or a pharmaceutically acceptable salt, hydrate or solvate thereof.

10. The compound of claim 6 having structural Formula (IX):

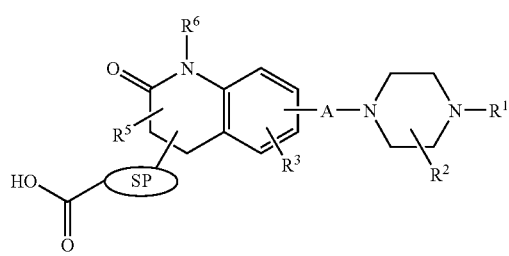

Formula IX or a pharmaceutically acceptable salt, hydrate or solvate thereof.

11. The compound of claim 7 having structural Formula (X):

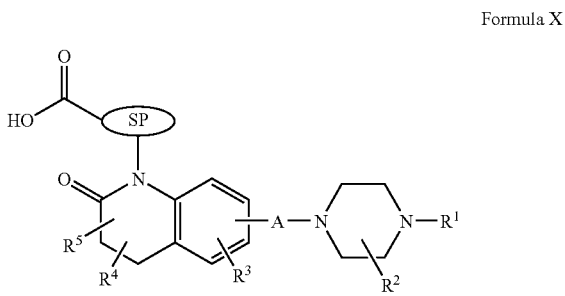

Formula X or a pharmaceutically acceptable salt, hydrate or solvate thereof.

12. The compound of claim 1, wherein X is O.

13. The compound of claim 1, wherein X is NH.

14. The compound of claim 1, wherein the spacer is aryloxyalkyl.

15. The compound of claim 1, wherein $R^2$-$R^6$ are hydrogen, and $R^7$ is alkyl.

16. The compound of claim 1, which is Compound 8,

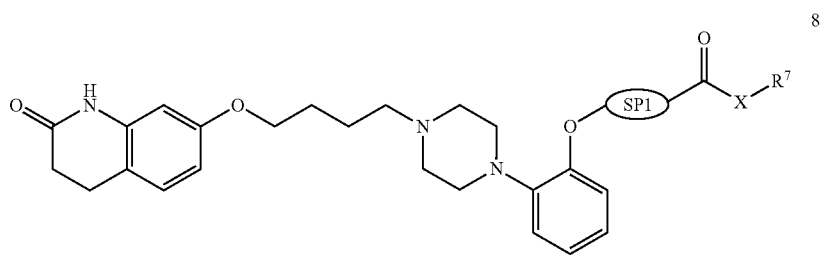

8 wherein SP1 is alkyl, and X is O or NH.

17. A pharmaceutical composition comprising the compound of claim 1, or a pharmaceutically acceptable salt thereof, and a pharmaceutically acceptable vehicle.

18. A method of treating a disease in a patient, the method comprising:
administering to a patient in need thereof the pharmaceutical composition of claim 17, wherein the disease is schizophrenia, acute manic, bipolar disorder, or depression.

19. The method of claim 18, wherein the administering is oral, mucosal, rectal, parenteral, transdermal, or subcutaneous administration.

20. The method of claim 18, wherein the disease is schizophrenia.

21. The method of claim 18, wherein the disease is bipolar disorder.

22. The method of claim 18, wherein the disease is depression.

23. The method of claim 18, wherein the disease is acute manic.

* * * * *